(12) United States Patent
Holtcamp et al.

(10) Patent No.: US 9,024,034 B2
(45) Date of Patent: May 5, 2015

(54) METATHESIS CATALYSTS AND PROCESSES FOR USE THEREOF

(75) Inventors: Matthew W. Holtcamp, Huffman, TX (US); Matthew S. Bedoya, Humble, TX (US); Catherine A. Faler, Houston, TX (US); Caol P. Huff, Houston, TX (US); John R. Hagadorn, Houston, TX (US); Renuka N. Ganesh, Baltimore, MD (US); Ravindra Ganesh, legal representative, Baltimore, MD (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 75 days.

(21) Appl. No.: 12/939,024

(22) Filed: Nov. 3, 2010

(65) Prior Publication Data

US 2011/0112302 A1 May 12, 2011

Related U.S. Application Data

(63) Continuation-in-part of application No. 12/705,136, filed on Feb. 12, 2010, now Pat. No. 8,237,003.

(60) Provisional application No. 61/314,388, filed on Mar. 16, 2010, provisional application No. 61/259,521, filed on Nov. 9, 2009.

(51) Int. Cl.
*C07F 15/00* (2006.01)
*C07C 6/04* (2006.01)
*B01J 31/22* (2006.01)

(52) U.S. Cl.
CPC .............. *C07F 15/0046* (2013.01); *C07C 6/04* (2013.01); *C07C 2531/22* (2013.01); *B01J 31/2208* (2013.01); *B01J 31/2273* (2013.01); *B01J 31/2278* (2013.01); *B01J 2531/0261* (2013.01); *B01J 2531/821* (2013.01); *B01J 2531/825* (2013.01)

(58) Field of Classification Search
CPC ................................... C07F 15/0046
USPC ....................................... 548/103
See application file for complete search history.

(56) References Cited

U.S. PATENT DOCUMENTS

| | | | |
|---|---|---|---|
| 4,048,245 | A | 9/1977 | Pollitzer et al. |
| 4,130,597 | A | 12/1978 | Wilhelm |
| 4,133,839 | A | 1/1979 | Hayes |
| 4,545,941 | A | 10/1985 | Rosenburg |
| 6,900,347 | B2 | 5/2005 | Paulson et al. |
| 7,119,216 | B2 | 10/2006 | Newman et al. |
| 7,205,424 | B2 | 4/2007 | Nolan |
| 7,268,242 | B2 | 9/2007 | Pederson et al. |
| 7,312,331 | B2 | 12/2007 | Bertrand et al. |
| 7,579,511 | B1 | 8/2009 | Dakka |
| 7,632,772 | B2 | 12/2009 | Zhan |
| 2005/0070750 | A1 | 3/2005 | Newman et al. |
| 2006/0287450 | A1 | 12/2006 | Kohler et al. |
| 2007/0043180 | A1 | 2/2007 | Zhan |
| 2007/0270621 | A1 | 11/2007 | Millis et al. |
| 2008/0027194 | A1 | 1/2008 | Schrodi |
| 2008/0064891 | A1 | 3/2008 | Lee |
| 2008/0269525 | A1 | 10/2008 | Bertrand et al. |
| 2009/0048459 | A1 | 2/2009 | Tupy et al. |
| 2009/0069516 | A1 | 3/2009 | Obrecht et al. |
| 2009/0187035 | A1 | 7/2009 | Ko et al. |
| 2009/0259065 | A1 | 10/2009 | Abraham et al. |
| 2010/0022789 | A1 | 1/2010 | Mignani et al. |
| 2010/0174068 | A1 | 7/2010 | Grela et al. |
| 2011/0112349 | A1 | 5/2011 | Holtcamp et al. |

FOREIGN PATENT DOCUMENTS

| | | |
|---|---|---|
| EP | 2 151 446 | 2/2010 |
| JP | 58-154594 | 9/1983 |
| WO | WO 00/71554 | 11/2000 |
| WO | 03/097234 | 11/2003 |
| WO | WO 2004/062763 | 7/2004 |
| WO | WO 2006/138166 | 12/2006 |
| WO | 2008-000644 | 1/2008 |
| WO | WO 2008/010961 | 1/2008 |
| WO | WO 2008/046106 | 4/2008 |
| WO | WO 2008/095785 | 8/2008 |
| WO | WO 2008/125568 | 10/2008 |
| WO | WO 2008/140468 | 11/2008 |
| WO | WO 2009/009597 | 1/2009 |
| WO | WO 2009/126831 | 10/2009 |
| WO | 2011-119778 | 9/2011 |
| WO | WO2011/056874 | 12/2011 |

OTHER PUBLICATIONS

Ledoux et al. "N,N'-dialkyl- and N-alkyl-N-mesityl-substituted N-heterocyclic carbenes as ligands in Grubbs catalysts" Chemistry—A European Journal, 2006, vol. 12, pp. 4654-4661.*

Vehlow et al. "Alternating Copolymerizations Using a Grubbs-Type Initiator with an Unsymmetrical, Chiral N-Heterocyclic Carbene Ligand" Angewandte Chemie International Edition, 2008, vol. 47, pp. 2615-2618.*

Fournier et al. "A Highly Active Chiral Ruthenium-Based Catalyst for Enantioselective Olefin Metathesis" Organometallics, 2007, vol. 26, pp. 2945-2949.*

Chung et al. "Olefin Metathesis Catalyst: Stabilization Effect of Backbone Substitutions of N-Heterocyclic Carbene" Organic Letters, 2008, vol. 10, pp. 2693-2696.*

(Continued)

*Primary Examiner* — Joseph Kosack

(57) ABSTRACT

This invention relates to a metathesis catalyst compound comprising an asymmetrically substituted N-heterocyclic carbene (NHC) metathesis catalyst and a process to make linear alpha-olefins comprising contacting a feed material and an optional alkene (such as ethylene) with said catalyst, where the feed material is a triacylglyceride, fatty acid, fatty acid alkyl ester, and/or fatty acid ester, typically derived from biodiesel.

32 Claims, No Drawings

(56) References Cited

OTHER PUBLICATIONS

Savoie et al. "Improved Chiral Olefin Metathesis Catalysts: Increasing the Thermal and Solution Stability via Modification of a C1-Symmetrical N-Heterocyclic Carbene Ligand" Advanced Synthesis & Catalysis, 2009, vol. 351, pp. 1826-1832.*

Arnold et al., "*Asymmetric Lithium(I) and Copper (II) Alkoxy-N-Heterocyclic Carbene Complexes; Crystallographic Charaterisation and Lewis Acid Catalysis*", Chemical Communications, 2004, pp. 1612-1613.

Arnold et al., "Anionic Amido N-Heterocyclic Carbenes; Synthesis of Covalently Tethered Lanthanide-Carbene Complexes", Angewandte Chemie International Edition, 2003, vol. 42, pp. 5981-5984.

De Fremont et al., "*Cationic NHC-Gold(I) Complexes: Synthesis, Isolation and Catalytic Activity*", Journal of Organometallic Chemistry, 2009, vol. 694, pp. 551-560.

Frankel et al., "*A Homopletic Carbene-Lithium Complex*", Angewandte Chemie International Edition, 2001, vol. 40, No. 10, pp. 1907-1910.

Hahn et al., "*Heterocyclic Carbenes: Synthesis and Coordination Chemistry*", Angewandte Chemie International Edition, 2008, vol. 47, pp. 3122-3172.

Allen et al., "*Well-Defined Silica-Supported Olefin Metathesis Catalysts*", Organic Letters, 2009, vol. 11, No. 6, pp. 1261-1264.

Blum et al., "*Synthesis of N-Heterocyclic Carbene-Containing Metal Complexes from 2-(Pentafluorophenyl)Imidazolidines*", Organometallics, 2007, vol. 26, No. 8, pp. 2122-2124.

Chung et al., "*Olefin Metathesis Catalyst: Stabilization Effect of Backbone Substitutions of N-Heterocyclic Carbene*", Organic Letters, 2008, vol. 10, No. 13, pp. 2693-2696.

Dinger et al., "*Adamantyl-Substituted N-Heterocyclic Carbene Ligands in Second-Generation Grubbs-Type Metathesis Catalysts*", Organometallics, 2003, vol. 22, No. 25, pp. 5291-5296.

Herrmann et al., "*N-Heterocyclic Carbenes[+]: Generation under Mild Conditions and Formation of Groups 8-10 Transition Metal Complexes Relevant to Catalysts*", Chemistry, A European Journal, 1996, vol. 2, No. 7, pp. 772-780.

Ledoux et al., "*Comparative Investigation of Hoveyda-Grubbs Catalysts Bearing Modified N-Heterocyclic Carbene Ligands*", Advanced Synthesis & Catalysis, 2007, vol. 349, No. 10, pp. 1692-1700.

Ledoux et al., "*N-N'-Dialkyl- and N-Alkyl-N-Mesityl-Substituted N-Heterocyclic Carbenes as Ligands in Grubbs Catalysts*", Chemistry, A European Journal, 2006, vol. 12, No. 17, pp. 4654-4661.

Leuthaußer et al., "*π-Face Donor Properties of N-Heterocyclic Carbenes in Grubbs II Complexes*", Chemistry, A European Journal, 2008, vol. 14, No. 18, pp. 5465-5481.

Lichtenheldt et al., "*Alternating Ring-Opening Metathesis Copolymerization by Grubbs-Type Initiators with Unsymmetrical N-Heterocyclic Carbenes*", Chemistry, A European Journal, 2009, vol. 15, No. 37, pp. 9451-9457.

Santhosh Kumar et al., "*Factors Relevant for the Regioselective Cyclopolymerization of 1,6-Heptadiynes, N,N-Dipropargylamines, N,N-Dipropargylammonium Salts, and Dipropargyl Ethers by RuIV-Alklidene-Based Metathesis Initiators*", Journal of the American Chemical Society, 2009, vol. 131, No. 1, pp. 387-395.

Sußner et al., "*π-Face Donor Properties of N-Heterocyclic Carbenes*", Chemical Communications, 2005, No. 43, pp. 5417-5419.

Tiede et al., "*Highly Active Chiral Ruthenium-based Metathesis Catalysts Through a Monosubstitution in the N-Heterocyclic Carbene*", Angewandte Chemie, International Edition, 2010, vol. 49, No. 23, pp. 3972-3975.

Vehlow et al., "*Alternating Copolymerizations Using a Grubbs-Type Initiator with an Unsymmetrical, Chiral N-Heterocyclic Carbene Ligand*", Angewandte Chemie, International Edition, 2008, vol. 47, No. 14, pp. 2615-2618.

Vehlow et al., "*Deactivation of Ruthenium Olefin Metathesis Catalysts Through Intromolecular Carbene-Arene Bond Formation*", Angewandte Chemie, International Edition, 2007, vol. 46, No. 42, pp. 8082-8085.

Vougioukalakis et al., "*Ruthenium-Based Olefin Metathesis Catalysts Coordinated with Unsymmetrical N-Heterocyclic Carbene Ligands: Synthesis, Structure, and Catalytic Activity*", Chemistry, A European Journal, 2008, vol. 14, No. 25, pp. 7545-7556.

Vougioukalakis et al., "*Ruthenium Olefin Metathesis Catalysts Bearing an N-Fluorophenyl-N-Mesityl-Substituted Unsymmetrical N-Heterocyclic Carbene*", Organometallics, 2007, vol. 26, No. 9, pp. 2469-2472.

Xu et al., "*Development of Building Blocks for the Synthesis of N-Heterocyclic Carbene Ligands*", Organic Letters, 2005, vol. 7, No. 21, pp. 4605-4608.

Alder et al., "*Complexation of Stable Carbenes With Alkali Metals*", Chemical Communications, 1999, No. 3, pp. 241-242.

Anderson et al., "*Synthesis and Reactivity of Olefin Metathesis Catalysts Bearing Cyclic (Alkyl)(Amino)Carbenes*", Angewandte Chemie, International Edition, 2007, vol. 46, No. 38, pp. 7262-7265.

Anderson et al., "*Kinetic Selectivity of Olefin Metathesis Catalysts Bearing Cyclic (Alkyl)(Aminoi)Carbenes*", Organometallics, 2008, vol. 27, No. 4, pp. 563-566.

Arduengo III et al., "*Carbene-Lithium Interactions*", Chemistry Letters, 1999, vol. 28, No. 10, pp. 1021-1022.

Arduengo et al., "*Carbene Adducts of Magnesium and Zinc*", Journal of Organometallic Chemistry, 1993, vol. 462, No. 1-2, pp. 13-18.

Arduengo et al., *Adducts of Carbenes with Group II and XII Metallocenes*, Organometallics, 1998, vol. 17, No. 15, pp. 3375-3382.

Arnold et al., "*Magnesium and Zinc Complexes of Functionalised, Saturated N-heterocyclic Carbene Ligands: Carbene lability and Functionalisation, and Lactide Polymerisation Catalysis*", Journal of Chemical Society, Dalton Transactions, 2009, No. 35, pp. 7236-7247.

Arrowsmith et al., "*AHydride-Rich Magnesium Cluster*", Angewandte Chemie, International Edition, 2009, vol. 48, No. 22, pp. 4013-4016.

Azizoglu et al., "*Substituent Effects on the Ring-Opening Mechanism of Lithium Bromocyclopropylidenoids to Allenes*", Journal of Organic Chemistry, 2008, vol. 73, No. 21, pp. 8182-8188.

Berthelot et al., "*Gas-Phase Reactivity of (C5H5Mg)+ Complexes: An Experimental and Theoretical Study*", Journal of Physical Chemistry. A molecules, Spectroscopy, Kinetics, Enironment and General Theory, 1998, vol. 102, No. 29, pp. 6025-6034.

Bourisson et al., "*Stable Carbenes*", Chemical Reviews, 2000, vol. 100, No. 1, pp. 39-91.

Burdett et al., "*Renewable Monomer Feedstocks via Olefin Metathesis: Fundamental Mechanistic Studies of Methyl Oleate Ethenolysis with the First-Generation Grubbs Catalyst*", Organometallics, 2004, vol. 23, No. 9, pp. 2027-2047.

Diez-Gonzalez et al., "*N-Heterocyclic Carbenes in Late Transition Metal Catalysis*", Chemical Reviews, 2009, vol. 109, No. 8, pp. 3612-3676.

Dragutan et al., "*Ruthenium Indenylidene Complexes: Metathesis Catalysts With Enhanced Activity*", Platinum Metals Rev. 2005, vol. 49, Issue 1, p. 33-40.

Furstner et al., "*Ruthenium Carbene Complexes with N,N'-Bis(mesityl)imidazol-2-ylidene Ligands: RCM Catalysts of Extended Scope*", J. Org. Chem., 2000, vol. 65, Issue 7, pp. 2204-2207.

Grant No. DE-FG36-04GO14016, "*Platform Chemicals from an Oilseed Biorefinery,*" awarded by the Department of Energy, Final Technical Report, Nov. 30, 2006.

Hermann et al., "*Heterocyclic Carbenes: A High-Yielding Synthesis of Novel, Functionalized N-Heterocyclic Carbenes in Liquid Ammonia*", Chemistry, A European Journal, 1996, vol. 2, No. 12, pp. 1627-1636.

Hoveyda et al., "*A Recyclable Ru-Based Metathesis Catalyst*", Journal of American Chemical Society, 1999, vol. 121, pp. 791-799.

Kingsbury et al., "*A Recyclable Ru-Based Metathesis Catalyst*", J. Am. Chem. Soc., 1999, vol. 121, pp. 791-799.

Jazzar et al., "*A New Synthetic Method for the Preparation of Protonated-NHCs and Related Compounds*", Journal of Organometallic Chemistry, 2006, vol. 691, No. 14, pp. 3201-3205.

(56) References Cited

OTHER PUBLICATIONS

Jazzar et al., "*Intramolecular "Hydroiminiumation" of Alkenes: Application to the Synthesis of Conjugate Acids of Cyclic Alkyl Amino Carbenes (CAACs)*", Angewandte Chemie, International Edition, 2007, vol. 46, No. 16, pp. 2899-2902.

Lavallo et al., "*A Rigid Cyclic (Alkyl)amino)carbine) Ligand Leads to Isolation of Low-Coordinate Transition-Metal Complexes*", Angew. Chem. Int. Ed., 2005, vol. 44, No. 44, pp. 7236-7239.

Lavallo et al., "*Isolation of Cyclopropenylidene-Lithium Adducts: The Weiss-Yoshida Reagent*", Angewandte Chemie, International Edition, 2006, vol. 45, No. 40, pp. 6652-6655.

Lavallo et al., "*Stable Cyclic (Alkyl)(Amino)Carbenes as Rigid or Flexible, Bulky, Electron-Rich Ligands for Transition-Metal Catalysts: A quaternary Carbon Atom Makes the* ", Angew. Chem. Int. Ed., 2005, vol. 44, No. 35, pp. 5705-5709.

Rybak et al., "*Metathesis a Versatile Tool in Olechemistry*", Eur. J. Lipid Sci. Technol, Weinheim, 2008, vol. 110, pp. 797-804.

Scholl et al., "*Synthesis and Activity of a new Generation of Ruthenium-Based Olefin Metathesis Catalysts Coordinated with 1,3-Diesityl-4, 5-Dihydroimidazol-2-ylidene Ligands*" Org. Letters, 1999, vol. 1, pp. 953-956.

Schrodi et al., "*Ruthenium Olefin Metathesis Catalysts for the Ethenolysis of Renewable Feedstocks*", Clean: Soil, Air, Water, vol. 36, Issue 8, pp. 669-673.

Schumann et al., "*Metallocenes of the Alkaline Earth Metals and Their Carbene Complexes*", Journal of Organometallic Chemistry, 2001, vol. 617-618, pp. 588-600.

Sigal et al., "*Are Disilacyclopropylidenes and Their Carbenoids Good Precursors for the Unknown 1, 3-Disilaallenes?*", Journal of Organometallic Chemistry, 2001, vol. 636, No. 1-2, pp. 148-156.

Stasch et al., "*Synthesis and Characterization of Alkynyl Complexes of Groups 1 and 2*", Chemistry, An Asian Journal, 2009, vol. 4, No. 9, pp. 1451-1457.

Tamm et al., "*Pentacarbonylchromium(0) and -tungsten(0) Complexes with the Bis(Diisopropylamino) Cyclopropenylidene Ligand*", Journal of Organometallic Chemistry, 1995, vol. 501, No. 1, pp. 309-313.

Vehlow et al., "*Ruthenium Metathesis Catalysts with Saturated Unsymmetrical N-Heterocyclic Carbene Ligands*", Organometallics, 2006, vol. 25, No. 1, pp. 25-28.

Assay, et al., "*Cyclic(amino)[bis(ylide)]carbene as an Anionic Bidentate Ligand for Transition-metal Complexes*", Inorg. Chem., 2008, vol. 47, pp. 3949-3951.

Huang et al., "*Kinetic and Thermodynamic Study of Syn-anti Isomerization of Nickel Complexes Bearing Aminio-linked N-heterocyclic Carbene Ligands: The Effect of the Pendant Arm of the NHC*", Organometallics, 2009, vol. 28, pp. 4316-4323.

Shih et al., "*Synthesis and Structure of an Amino-linked N-heterocyclic Carbene and the Reactivity of its Aluminum Adduct*", Organometallics, 2009, vol. 28, 1060-1067.

Pierre-Andre Fournier, et al., *A Highly Active Chiral Ruthenium-Based Catalyst for Enantioselective Olefin Metathesis*, Organometallics, vol. 26, No. 12, Jun. 4, 2007, pp. 2945-2949.

Daryl P. Allen, et al., *Well-Defined Silica-Supported Olefin Metathesis Catalysts*, Organic Letters, vol. 11, No. 6, 2009, pp. 1261-1264.

Jolaine Savoie, et al., *Improved Chiral Olefin Metathesis Catalysts: increasing the Thermal and Solution Stability via Modification of a C1-Symmetrical N-Heterocyclic Carbene Ligand*, Advanced Synthesis Catal., 7/21,2009, pp. 1826-1832.

\* cited by examiner

METATHESIS CATALYSTS AND PROCESSES FOR USE THEREOF

PRIORITY CLAIM

This invention claims priority to and the benefit of U.S. Ser. No. 61/314,388, filed Mar. 16, 2010.
This invention is a continuation-in-part of U.S. Ser. No. 12/705,136, filed Feb. 12, 2010.
This invention claims priority to and the benefit of U.S. Ser. No. 61/259,521, filed Nov. 9, 2009.
This invention claims priority to and the benefit of U.S. Ser. No. 61/314,388, filed Mar. 16, 2010.
This invention claims priority to and the benefit of U.S. Ser. No. 12/705,136, filed Feb. 12, 2010.
This invention claims priority to and the benefit of U.S. Ser. No. 61/259,521, filed Nov. 9, 2009.

STATEMENT OF RELATED APPLICATIONS

This invention is related to U.S. Ser. No. 12/939,054, filed on Nov. 3, 2010 (now granted as U.S. Pat. No. 8,063,232), and claiming priority to USSN 61/259,514, filed Nov. 9, 2009. This invention is also related to, U.S. Ser. No. 12/939,063, filed on Nov. 3, 2010 and claiming priority to U.S. Ser. No. 61/259,521, filed Nov. 9, 2009.

FIELD OF THE INVENTION

This invention relates to metathesis catalyst compounds and processes for the use thereof.

BACKGROUND OF THE INVENTION

The cross-metathesis of two reactant olefins, where each reactant olefin comprises at least one unsaturation site, to produce new olefins which are different from the reactant olefins is of significant commercial importance. The cross-metathesis reaction is usually catalyzed by one or more catalytic metals, usually one or more transition metals.

One such commercially significant application is the cross-metathesis of ethylene and internal olefins to produce alpha-olefins, which is generally referred to as ethenolysis. In particular, the cross-metathesis of ethylene and an internal olefin to produce linear alpha-olefins (LAOS) is of particular commercial significance. LAOs are useful as monomers or comonomers in certain (co)polymers (polyalphaolefins or PAOs) and/or as intermediates in the production of epoxides, amines, oxo alcohols, synthetic lubricants, synthetic fatty acids and alkylated aromatics. Olefins Conversion Technology™, based upon the Phillips Triolefin Process, is an example of an ethenolysis reaction converting ethylene and 2-butene into propylene. These processes use heterogeneous catalysts, such as tungsten and rhenium oxides, which have not proven effective for internal olefins containing functional groups such as cis-methyl oleate, a fatty acid methyl ester.

Methods for the production of polyalpha-olefins are typically multi-step processes that often create unwanted by-products and waste of reactants and energy. Full range linear alpha-olefins plants are petroleum-based, are inefficient, and result in mixtures of oligomerization products that typically yield Schulz-Flory distributions producing large quantities of undesirable materials. In recent years there have been new technologies implemented to produce "on purpose" linear alpha-olefins such 1-hexene and 1-octene through chromium-based selective ethylene trimerization or tetramerization catalysts. Alternatively, 1-octene has been produced via the telomerization of butadiene and methanol. Similar strategies are not currently available for the production of 1-decene.

1-decene is a co-product typically produced in the cross-metathesis of ethylene and methyl oleate. Alkyl oleates are fatty acid esters that can be major components in biodiesel produced by the transesterification of alcohol and vegetable oils or animal fats. Vegetable oils containing at least one site of unsaturation include canola, soybean, palm, peanut, mustard, sunflower, tung, tall, perilla, grapeseed, rapeseed, linseed, safflower, pumpkin corn and many other oils extracted from plant seeds. Alkyl erucates similarly are fatty acid esters that can be major components in biodiesel. Useful biodiesel compositions are those which typically have high concentrations of oleate and erucate esters. These fatty acid esters preferably have one site of unsaturation such that cross-metathesis with ethylene yields 1-decene as a co-product.

Biodiesel is a fuel prepared from renewable sources, such as plant oils or animal fats. To produce biodiesel, triacylglycerides ("TAG"), the major compound in plant oils and animal fats, are converted to fatty acid alkyl esters ("FAAE," i.e., biodiesel) and glycerol via reaction with an alcohol in the presence of a base, acid, or enzyme catalyst. Biodiesel fuel can be used in diesel engines, either alone or in a blend with petroleum-based diesel, or can be further modified to produce other chemical products.

Cross-metathesis catalysts reported thus far for the ethenolysis of methyl oleate are typically ruthenium-based catalysts bearing phosphine or carbene ligands. Dow researchers in 2004 achieved catalysts turnovers of approximately 15,000 using the $1^{st}$ generation Grubb's catalyst, bis(tricyclohexylphosphine)benzylidene ruthenium(IV) dichloride, (*Organometallics* 2004, 23, p. 2027). Researchers at Materia, Inc. have reported turnover numbers up to 35,000 using a ruthenium catalyst containing a cyclic alkyl amino carbene ligand, (WO 2008/010961). These turnovers were obtained with a catalyst reportedly too expensive for industrial consideration due to high costs associated with the catalysts being derived from a low yielding synthesis (See, Final Technical Report entitled "Platform Chemicals from an Oilseed Biorefinery" grant number DE-FG36-04GO14016 awarded by the Department of Energy). Additionally, the introduction of chelating isopropoxybenzylidene ligands has led to ruthenium catalysts with improved activities for metathesis reactions (*J. Am. Chem. Soc.* 1999, 121, p. 791). However, these ruthenium alkylidene catalysts are usually prepared by the reaction of ruthenium species with diazo compounds. The concerns associated with industrial scale reactions comprising diazo compounds have led to increased efforts to prepare ruthenium alkylidenes via alternate synthetic routes, such as using terminal alkynes or propargyl alcohols.

The synthesis of $RuCl_2(PCy_3)_2$(3-phenylindenylene) has proven useful in providing an easy route to ruthenium alkylidenes which avoids costly diazo preparations (Platinum Metals Rev. 2005, 49, p. 33). Also, Furstner et al., *J. Org. Chem.*, 2000, 65, pp. 2204-2207, have prepared (N,N'-bis(mesityl)imidazol-2-ylidene)$RuCl_2$(3-phenylindenylene). However, these types of complexes have not proven effective in ethenolysis reactions.

Unsymmetrical N-heterocyclic carbene ligands have been prepared by Blechert and coworkers and complexed to ruthenium alkylidenes to form active metathesis catalysts (*Organometallics* 2006, 25, pp. 25-28). It was hypothesized that these complexes would give improved activity to that of the symmetrical analogs previously prepared by Grubbs and coworkers (*Org. Lett.* 1999, 1, pp. 953-956). These complexes were tested for catalytic activity in ring closing and cross-metathesis reactions. However, the catalysts were reported to be similar in activity to the symmetrical analogs, namely the Grubbs catalyst, $2^{nd}$ generation (1,3-bis-(2,4,6-trimethylphenyl)-2-(imidazolidinylidene) (dichlorophenyl-methylene)(tricyclohexylphosphine)ruthenium) and the expected improved activities were not observed.

In order to obtain an economically viable process for 1-decene production via the cross-metathesis of ethylene and biodiesel (derived from animal or vegetable oils), higher activity catalysts must be discovered. Thus there is a need for higher activity processes that produce desired products and co-products in commercially desirable ratios.

There remains a need for catalysts which demonstrate high activity and selectivity in ethenolysis which are capable of being synthesized by both mild and affordable synthetic routes. The instant invention's metathesis catalyst compounds provide both a mild and commercially economical and an "atom-economical" route to desirable olefins, in particular alpha-olefins, which in turn may be useful in the preparation of PAOs. More particularly, the instant invention's metathesis catalyst compounds demonstrate improved activity and selectivity towards ethenolysis products in ethylene cross-metathesis reactions.

The inventors have found that symmetrically substituted N-heterocyclic carbene ligands linked to ruthenium alkylidenes, though known to be cross-metathesis catalysts, tend to have low activity in the ethenolysis of methyl oleate. Surprisingly, an asymmetrically substituted N-heterocyclic carbene ligand linked to a ruthenium alkylidene yielded a catalyst that was more active than the symmetrical analog and very selective towards the ethenolysis of methyl oleate yielding 1-decene and methyl-9-decenoate.

Other references of interest include: U.S. Pat. Nos. 7,119,216; 7,205,424; US 2007/0043180; WO 2006/138166; WO 2008/010961; US 2007/0043180; U.S. Pat. No. 7,268,242; WO 2008/125568; WO 2008/046106; WO 2008/095785; WO 2008/140468; U.S. Pat. No. 7,312,331; and WO 2008/010961.

Other references of interest also include: a) "Synthesis and Reactivity of Olefin Metathesis Catalysts Bearing Cyclic (Alkyl)(Amino)Carbenes" Anderson et al., Angew. Chem. Int. Ed. 2007, 46, pp. 7262-7265; b) "Intramolecular 'Hydroiminiumation' of Alkenes: Applications to the Synthesis of Conjugate Acids of Cyclic Alkyl Amino Carbenes (CAACs)" Jazzar et al., Angew. Chem. Int. Ed. 2007, 46, pp. 2899-2902; c) "Kinetic Selectivity of Olefin Metathesis Catalysts Bearing Cyclic (Alkyl)(Amino)Carbenes" Anderson et al., Organometallics, 2008, 27, pp. 563-566; d) "A New Synthetic Method for the Preparation of Protonated-NHCs and Related Compounds" Jazzar et al., J. Organometallic Chemistry 691, 2006, pp. 3201-3205; e) "A Rigid Cyclic (Alkyl)(Amino)carbene Ligand Leads to Isolation of Low-Coordinate Transition Metal Complexes" Lavallo et al., Angew. Chem. Int. Ed., 2005, 44, pp. 7236-7239; f) "Stable Cyclic (Alkyl)(Amino)carbenes as Rigid or Flexible, Bulky Electron-Rich Ligands for Transition Metal Catalysts: A Quaternary Carbon Atom Makes the Difference" Angew. Chem. Int. Ed., 2007, 44, pp. 5705-5709; g) "Synthesis and Activity of a New Generation of Ruthenium-Based Olefin Metathesis Catalysts Coordinated with 1,3-Dimesityl-4,5-dihydroimidazol-2-ylidene Ligands" Org. Letters, 1999, 1, pp. 953-956.

SUMMARY OF THE INVENTION

This invention relates to an asymmetrically substituted N-heterocyclic carbene (NHC) metathesis catalyst and process for use thereof in the production of olefins, where the metathesis catalyst is represented by the following formula:

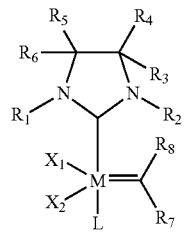

where:
M is a Group 8 metal; preferably Ru or Os;
$X_1$ and $X_2$ are, independently, any anionic ligand, or $X_1$ and $X_2$ may be joined to form a dianionic group and may form a single ring of up to 30 non-hydrogen atoms or a multinuclear ring system of up to 30 non-hydrogen atoms;
L is a heteroatom or heteroatom-containing ligand; preferably the heteroatom is N, O, P, or S; preferably P; optionally L may be joined to $R_7$ and/or $R_8$;
and $R_1$, $R_2$, $R_3$, $R_4$, $R_5$, $R_6$, $R_7$, and $R_8$ are, independently, hydrogen or a $C_1$ to $C_{30}$ substituted or unsubstituted hydrocarbyl;
wherein any two adjacent R groups may form a single ring of up to 8 non-hydrogen atoms or a multinuclear ring system of up to 30 non-hydrogen atoms; and
wherein $R_1$ and $R_2$ are dissimilar to each other.

In alternate embodiments, when $R_7$ and $R_8$ form an unsubstituted phenyl group and $R_1$ is mesityl, then $R_2$ is not methyl or ethyl, preferably $R_2$ is hydrogen or $C_1$ to $C_{30}$ substituted hydrocarbyl, or a $C_3$ to $C_{30}$ unsubstituted hydrocarbyl (preferably a $C_4$ to $C_{30}$ unsubstituted hydrocarbyl, preferably a $C_5$ to $C_{30}$ unsubstituted hydrocarbyl, preferably a $C_6$ to $C_{30}$ unsubstituted hydrocarbyl).

DETAILED DESCRIPTION

The present invention comprises a novel metathesis catalyst compound useful for the cross-metathesis of olefins, and processes for the use thereof. More particularly, the present invention comprises a novel metathesis catalyst compound which comprises an asymmetrically substituted N-heterocyclic carbene group. Even more particularly, the present invention comprises a novel metathesis catalyst compound which demonstrates improved activity and selectivity towards ethenolysis products in ethylene cross-metathesis reactions.

This invention also relates to a process comprising contacting a feed oil (typically a triglyceride or seed oil) or derivative thereof (and optional alkene) with an olefin metathesis catalyst of the types described herein under conditions which yield an alpha-olefin. The feed oil may be esterified or trans-esterified with an alcohol prior to contacting with the olefin metathesis catalyst.

This invention also relates to a process comprising contacting a triacylglyceride or a derivative thereof with an optional alkene (such as ethylene) and an olefin metathesis catalyst of the types described herein under conditions which yield an alpha-olefin, typically yielding a linear alpha-olefin (such as 1-decene, 1-heptene, and/or 1-butene) and an ester or acid functionalized olefin.

This invention further relates to a process for producing alpha-olefins (preferably linear alpha-olefins) comprising contacting a triacylglyceride with an alcohol (such as methanol) to produce a fatty acid alkyl ester and thereafter contacting the fatty acid alkyl ester with an olefin metathesis catalyst of the types described herein (and optional alkene, such as ethylene) under conditions which yield an alpha-olefin (preferably a linear alpha-olefin, preferably 1-decene, 1-heptene, and/or 1-butene) and an ester or acid functionalized olefin.

This invention further relates to a process for producing alpha-olefins (preferably linear alpha-olefins) comprising contacting a triacylglyceride with water and/or an alkaline reactant (such as sodium hydroxide) to produce a fatty acid and thereafter contacting the fatty acid with an olefin metathesis catalyst of the types described herein (and optional alkene, such as ethylene) under conditions which yield an alpha-olefin (preferably a linear alpha-olefin, preferably 1-decene, 1-heptene, and/or 1-butene) and an acid functionalized olefin.

This invention further relates to contacting unsaturated fatty acids with an alkene (such as ethylene) in the presence of an olefin metathesis catalyst of the types described herein under conditions which yield an alpha-olefin (preferably a linear alpha-olefin, preferably 1-decene, 1-heptene, and/or 1-butene) and an acid functionalized olefin.

This invention further relates to contacting an unsaturated fatty acid ester with an alkene (such as ethylene) in the presence of an olefin metathesis catalyst of the types described herein under conditions which yield an alpha-olefin (preferably a linear alpha-olefin, preferably 1-decene, 1-heptene, and/or 1-butene) and an ester functionalized olefin.

This invention further relates to contacting an unsaturated fatty acid alkyl ester with an alkene (such as ethylene) in the presence of an olefin metathesis catalyst of the types described herein under conditions which yield an alpha-olefin (preferably a linear alpha-olefin, preferably 1-decene, 1-heptene, and/or 1-butene) and an ester functionalized olefin.

This invention also relates to a process to produce alpha olefins (preferably linear alpha olefins, preferably 1-decene, 1-heptene, and/or 1-butene) comprising contacting a metathesis catalyst of the types described herein with an alkene (preferably ethylene), and one or more fatty acid esters (preferably fatty acid methyl esters, preferably methyl oleate).

In a preferred embodiment, this invention relates to a process to produce alpha olefin (preferably linear alpha olefin, preferably 1-decene, 1-heptene, and/or 1-butene) comprising contacting a metathesis catalyst of the types described herein with an alkene (preferably ethylene), and one or more fatty acid esters (preferably fatty acid methyl esters, preferably methyl oleate) derived from biodiesel.

In a preferred embodiment, the olefin metathesis catalysts described herein may be combined directly with triacylglycerides, biodiesel, fatty acids, fatty acid esters, and/or fatty acid alkyl esters to produce alpha-olefins, preferably linear alpha olefins, preferably $C_4$ to $C_{24}$ alpha-olefins, preferably 1-decene, 1-heptene, and/or 1-butene.

In a preferred embodiment, a mixture of one or more triacylglyceride, biodiesel, fatty acids, and/or fatty acid esters is used to produce alpha-olefins, preferably linear alpha olefins, preferably $C_4$ to $C_{24}$ alpha-olefins, preferably $C_4$ to $C_{24}$ linear alpha-olefins. In a preferred embodiment, a mixture of alpha olefins, preferably linear alpha olefins, preferably 1-decene, 1-heptene, and/or 1-butene is produced.

Metathesis Catalysts

This invention relates to an asymmetrically substituted NHC metathesis catalyst compound represented by the following formula:

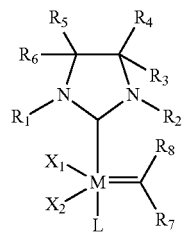

Formula (I)

where:

M is a Group 8 metal; preferably Ru or Os;

$X_1$ and $X_2$ are, independently, any anionic ligand, preferably a halogen (such as chlorine or bromine, preferably chlorine), an alkoxide or an alkyl sulfonate, or $X_1$ and $X_2$ may be joined to form a dianionic group and may form a single ring of up to 30 non-hydrogen atoms or a multinuclear ring system of up to 30 non-hydrogen atoms;

L is a heteroatom or heteroatom-containing group; preferably the heteroatom is N, O, P, or S; preferably P; optionally L may be joined to $R_7$ and/or $R_8$, preferably L is $L^*(R)_{q-1}$ when L is not bound to $R_7$ or $R_8$ or L is $L^*(R)_{q-2}$ when L is bound to $R_7$ or $R_8$, where q is 1, 2, 3, or 4 depending on the valence of $L^*$ (which may be 2, 3, 4, or 5) and $L^*$ is N, O, P, or S, preferably P and R is as defined for $R_3$;

and $R_1$, $R_2$, $R_3$, $R_4$, $R_5$, $R_6$, $R_7$, and $R_8$ are, independently, hydrogen or a $C_1$ to $C_{30}$ substituted or unsubstituted hydrocarbyl, preferably $R_1$, $R_2$, $R_3$, $R_4$, $R_5$, $R_6$, $R_7$, and $R_8$ are selected from the group consisting of methyl, ethyl, propyl butyl, hexyl, octyl, nonyl, decyl, undecyl, dodecyl, indenylene, substituted indenylene, phenyl, substituted phenyl, and the linear, branched and cyclic isomers thereof (including mesityl, 3,5,5-trimethylhexyl, cyclohexyl, methyl cyclohexyl, cyclododecyl, diisopropylphenyl, cyclopentyl, and norbornyl;

wherein any two adjacent R groups may form a single ring of up to 8 non-hydrogen atoms or a multinuclear ring system of up to 30 non-hydrogen atoms;

and wherein $R_1$ and $R_2$ are dissimilar to each other.

Preferably, any two adjacent R groups may form a fused ring having from 5 to 8 non-hydrogen atoms. Preferably, the non-hydrogen atoms are C and/or O. Preferably, the adjacent R groups form fused rings of 5 to 6 ring atoms, preferably 5 to 6 carbon atoms. By adjacent is meant any two R groups located next to each other, for example $R_7$ and $R_8$, can form a ring.

For purposes of this invention and claims thereto, a "Group 8 metal" is an element from Group 8 of the Periodic Table, as referenced by the IUPAC in *Nomenclature of Inorganic Chemistry: Recommendations*, G. J. Leigh, Editor, Blackwell Scientific Publications, 1990.

For purposes of this invention and claims thereto, a "substituted hydrocarbyl" is a radical made of carbon and hydrogen where at least one hydrogen is replaced by a heteroatom. For purposes of this invention and claims thereto, a "substituted alkyl or aryl" group is a radical made of carbon and hydrogen where at least one hydrogen is replaced by a heteroatom or a linear, branched, or cyclic substituted or unsubstituted hydrocarbyl group having 1 to 30 carbon atoms.

For purposes of this invention and claims thereto, "alkoxides" include those where the alkyl group is a $C_1$ to $C_{10}$ hydrocarbyl. The alkyl group may be straight chain or branched. Preferred alkoxides include a $C_1$ to $C_{10}$ alkyl group, preferably methyl, ethyl, propyl, butyl, or isopropyl. Preferred alkoxides include those where the alkyl group is a phenol, substituted phenol (where the phenol may be substituted with up to 1, 2, 3, 4, or 5 $C_1$ to $C_{12}$ hydrocarbyl groups) or a $C_1$ to $C_{10}$ hydrocarbyl, preferably a $C_1$ to $C_{10}$ alkyl group, preferably methyl, ethyl, propyl, butyl, or phenyl.

Preferred alkyl sulfonates are represented by the Formula (II):

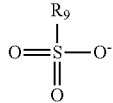

Formula (II)

where $R_9$ is a $C_1$ to $C_{30}$ hydrocarbyl group, fluoro-substituted hydrocarbyl group, chloro-substituted hydrocarbyl group, aryl group, or substituted aryl group, preferably a $C_1$ to $C_{12}$ alkyl or aryl group, preferably trifluoromethyl, methyl, phenyl, or para-methyl-phenyl.

In all embodiments herein, the invention relates to asymmetrically substituted NHC metathesis catalyst compounds wherein $R_1$ and $R_2$ are dissimilar to each other, causing asymmetry in the NHC ligand. For purposes of this invention and the claims thereto, dissimilar means that $R_1$ and $R_2$ differ by at least 1 non-hydrogen atom (preferably by at least 2, preferably at least 3, preferably by at least 4, preferably by at least 5 non-hydrogen atoms) or if $R_1$ and $R_2$ have the same number of non-hydrogen atoms, then they differ in structure or saturation, e.g., if one is cyclic then the other is linear; or if one is linear then the other is branched; or if one is saturated (such as cyclohexyl) then the other is aromatic (such as phenyl), etc. In particular embodiments, where $R_1$ and $R_2$ are dissimilar to each other, $R_1$ is an aromatic group, preferably phenyl, substituted phenyl, indenylenes, and substituted indenylenes; and $R_2$ is an aliphatic group, preferably methyl, ethyl, propyl, isopropyl, butyl, tert-butyl, pentyl, hexyl, cyclohexyl, cyclohexylmethyl, and so on. For example, in some embodiments, $R_1$ is a mesityl group and $R_2$ is a methyl group. In another embodiment, $R_1$ is a 2,6-diisopropylphenyl group and $R_2$ is a cyclohexylmethyl group. In yet another embodiment, $R_1$ is a 2,6-diisopropylphenyl group and $R_2$ is a propyl group. In alternate embodiments, when $R_7$ and $R_8$ form an unsubstituted phenyl group and $R_1$ is mesityl, then $R_2$ is not methyl or ethyl, preferably $R_2$ is hydrogen or $C_1$ to $C_{30}$ substituted hydrocarbyl, or a $C_3$ to $C_{30}$ unsubstituted hydrocarbyl (preferably a $C_4$ to $C_{30}$ unsubstituted hydrocarbyl, preferably a $C_5$ to $C_{30}$ unsubstituted hydrocarbyl, preferably a $C_6$ to $C_{30}$ unsubstituted hydrocarbyl). In a preferred embodiment, both $R_1$ and $R_2$ are a $C_3$ to $C_{30}$ unsubstituted or substituted hydrocarbyl (preferably a $C_4$ to $C_{30}$ unsubstituted or substituted hydrocarbyl, preferably a $C_5$ to $C_{30}$ unsubstituted or substituted hydrocarbyl, preferably a $C_6$ to $C_{30}$ unsubstituted or substituted hydrocarbyl). In another embodiment, one of $R_1$ and $R_2$ is aromatic (such as phenyl, mesityl, cyclopentyl, indenyl, norbornyl) and the other is a $C_3$ to $C_{30}$ unsubstituted or substituted hydrocarbyl (preferably a $C_4$ to $C_{30}$ unsubstituted or substituted hydrocarbyl, preferably a $C_5$ to $C_{30}$ unsubstituted or substituted hydrocarbyl, preferably a $C_6$ to $C_{30}$ unsubstituted or substituted hydrocarbyl).

In particular embodiments, the invention relates to asymmetrically substituted NHC metathesis catalyst compounds wherein $R_7$ or $R_8$ is not joined to L. In preferred embodiments, $R_7$ or $R_8$ is at least one of a phenyl, substituted phenyl, indenylene, and substituted indenylene group. For example, catalysts of the type below in Formula (III), where $R_7$ is not joined to L, where each G is independently, hydrogen, halogen, or $C_1$-$C_{30}$ substituted or unsubstituted hydrocarbyl, and $R_1$ and $R_2$ are dissimilar to each other are particularly useful herein.

In a preferred embodiment, this invention relates to a compound represented by the formula:

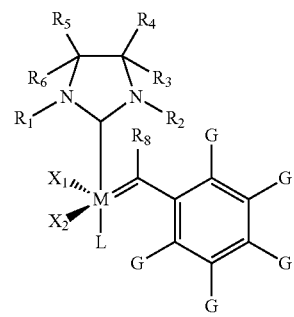

Formula (III)

where M, $X_1$, $X_2$, L, $R_1$, $R_2$, $R_3$, $R_4$, $R_5$, $R_6$, and $R_8$ are as defined in Formula (I) and G is independently, hydrogen, halogen, or $C_1$-$C_{30}$ substituted or unsubstituted hydrocarbyl. Preferably any two adjacent G groups may form a fused ring having from 5 to 8 non-hydrogen atoms. Preferably the non-hydrogen atoms are C and/or O. Preferably the adjacent G groups form fused rings of 5 to 6 ring atoms, preferably 5 to 6 carbon atoms.

In other particular embodiments, $R_7$ and $R_8$ are fused such that the $C(R_7)(R_8)$ group is a benzylidene, substituted benzylidene, indenylene, or substituted indenylene.

Even more particularly, a catalyst useful herein is (1-mesityl-3-methyl-2H-4,5-dihydroimidazol-2-ylidene)(tricyclohexylphosphine)-3-phenyl-1H-inden-1-ylidene ruthenium (II) dichloride, shown below in Formula (IV), wherein $R_1$ is a mesityl group, $R_2$ is a methyl group, $R_7$ and $R_8$ are fused to form a phenyl-substituted indenylene group which does not join to L, L is a tricyclohexylphosphine group (represented as $PCy_3$), and $X_1$ and $X_2$ are chloride groups. Ph=phenyl.

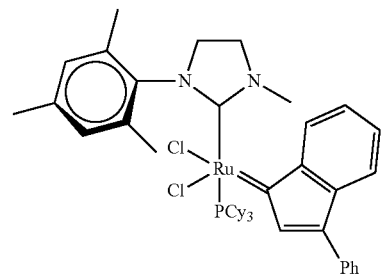

Formula (IV)

In other particular embodiments, the invention relates to asymmetrically substituted NHC metathesis catalyst compounds wherein a heteroatom of $R_7$ or $R_8$ is also joined to L, as represented below in Formula (V). In a preferred embodiment, this invention relates to a compound represented by the formula:

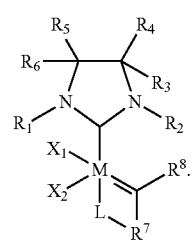

Formula (V)

where M, $X_1$, $X_2$, L, $R_1$, $R_2$, $R_3$, $R_4$, $R_5$, $R_6$, $R_7$, and $R_8$ are as defined in Formula (I). In preferred embodiments, $R_7$ or $R_8$ is at least one of a phenyl, substituted phenyl, indenylene, and substituted indenylene group. For example, catalysts of the type below in Formula (VI), where $R_7$ is a phenyl group joined to L, where each G is independently, hydrogen, halogen, or $C_1$-$C_{30}$ substituted or unsubstituted hydrocarbyl, and $R_1$ and $R_2$ are dissimilar to each other are particularly useful herein.

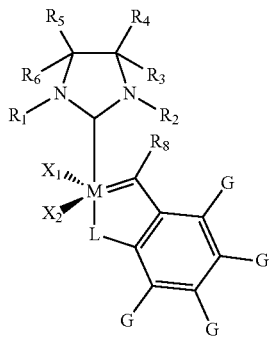

Formula (VI)

where M, $X_1$, $X_2$, L, $R_1$, $R_2$, $R_3$, $R_4$, $R_5$, $R_6$, and $R_8$ are as defined in Formula (I) and G is independently, hydrogen, halogen, or $C_1$-$C_{30}$ substituted or unsubstituted hydrocarbyl. Preferably any two adjacent G groups may form a fused ring having from 5 to 8 non-hydrogen atoms. Preferably the non-hydrogen atoms are C and/or O. Preferably the adjacent G groups form fused rings of 5 to 6 ring atoms, preferably 5 to 6 carbon atoms.

In other preferred embodiments, $R_7$ and $R_8$ are fused to form an indenylene group which is joined to L as shown in Formula (VII) below:

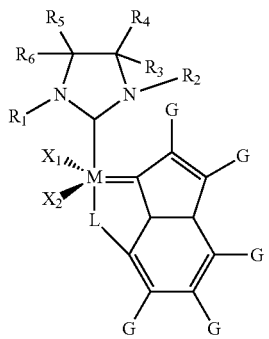

Formula (VII)

where M, $X_1$, $X_2$, L, $R_1$, $R_2$, $R_3$, $R_4$, $R_5$, and $R_6$ are as defined in Formula (I) and G is independently, hydrogen, halogen, or $C_1$-$C_{30}$ substituted or unsubstituted hydrocarbyl. Preferably any two adjacent G groups may form a fused ring having from 5 to 8 non-hydrogen atoms. Preferably the non-hydrogen atoms are C and/or O. Preferably the adjacent G groups form fused rings of 5 to 6 ring atoms, preferably 5 to 6 carbon atoms.

Even more particularly, a catalyst useful herein is 2-(i-propoxy)-5-(N,N-dimethylaminosulfonyl)phenylmethylene (1-cyclohexylmethyl-3-(2,6-diisopropylphenyl)-4,5-dihydro-1H-imidazole) ruthenium (II) chloride, shown below in Formula (VIII), wherein $R_1$ is a 2,6-diisopropylphenyl group, $R_2$ is a cyclohexylmethyl group, $R_7$ is a dimethylaminosulfonyl-substituted phenyl group which joins to L, L is an isopropoxy group, and $X_1$ and $X_2$ are chloride groups.

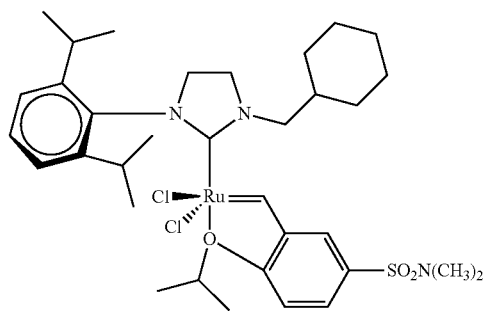

Formula (VIII)

Preferred metathesis catalysts useful herein include: 2-(i-propoxy)-5-(N,N-dimethyl-aminosulfonyl)phenylmethylene(1-cyclohexylmethyl-3-(2,6-diisopropylphenyl)-4,5-dihydro-1H-imidazole) ruthenium (II) chloride, (1-mesityl-3-methyl-2H-4,5-dihydroimidazol-2-ylidene) (tricyclohexylphosphine)-3-phenyl-1H-inden-1-ylidene ruthenium (II) dichloride, and mixtures thereof.

The catalyst compounds described herein may be synthesized as follows. The NHC precursor, as the imidazolium salt, can be synthesized as known in the art. For example, 2,6-diisopropylaniline ($R_1$) is reacted with 2-bromoethylamine hydrobromide at reflux for four days. The resulting diamine is condensed with a suitable reagent such as cyclohexylcarboxaldehyde ($R_2$) to give the imine. The resulting imine is reduced to the corresponding diamine using any suitable reducing agent, such as sodium borohydride. Treatment with triethyl formate and ammonium chloride yields the imidazolium salt. The imidazolium salt upon deprotonation with the appropriate base such as lithium bis(trimethylsilyl)amide generates the NHC ligand. This carbene can be reacted with ruthenium alkylidene complexes such as 2-(i-propoxy)-5-(N,N-dimethyl-aminosulfonyl)phenylmethylene(tricyclohexylphosphine) ruthenium dichloride to generate the asymmetrically substituted NHC ruthenium complex, 2-(i-propoxy)-5-(N,N-dimethyl-aminosulfonyl)phenylmethylene(1-cyclohexylmethyl-3-(2,6-diisopropylphenyl)-4,5-dihydro-1H-imidazole) ruthenium (II) chloride.

The resulting ruthenium alkylidene complex is an efficient catalyst or catalyst precursor towards for the cross-metathesis of ethylene and methyl oleate, a component of biodiesel, to generate with good selectivity 1-decene and methyl-9-decenoate.

Process

In a preferred embodiment, the metathesis catalysts described herein may be combined directly with feed oils, seed oils, triacylglycerides, biodiesel, fatty acids, fatty acid esters and/or fatty acid alkyl esters ("feed materials") to produce alpha-olefins, preferably linear alpha olefins, preferably $C_4$ to $C_{24}$ alpha-olefins, preferably $C_4$ to $C_{24}$ linear alpha-olefins, such as preferably 1-decene, 1-heptene, and/or 1-butene.

Typically, the molar ratio of alkene to unsaturated feed material (such as unsaturated fatty acid or fatty acid ester) is greater than about 0.8/1.0, preferably, greater than about 0.9/1.0. Typically, the molar ratio of alkene to feed material (such as unsaturated fatty acid or fatty acid ester) is less than about 3.0/1.0, preferably, less than about 2.0/1.0. Depending upon the specific reagents, other molar ratios may also be suitable.

With ethylene, for example, a significantly higher molar ratio can be used, because the self-metathesis of ethylene produces only ethylene again; no undesirable co-product olefins are formed. Accordingly, the molar ratio of ethylene to feed material (such as unsaturated fatty acid or fatty acid ester) may range from greater than about 0.8/1 to typically less than about 20/1.

The quantity of metathesis catalyst that is employed in the process of this invention is any quantity that provides for an operable metathesis reaction. Preferably, the ratio of moles of feed material (preferably fatty acid ester and/or fatty acid alkyl ester) to moles of metathesis catalyst is typically greater than about 10:1, preferably greater than about 100:1, preferably greater than about 1000:1, preferably greater than about 10,000:1, preferably greater than about 25,000:1, preferably greater than about 50,000:1, preferably greater than about 100,000:1. Alternately, the molar ratio of feed material (preferably fatty acid ester and/or fatty acid alkyl ester) to metathesis catalyst is typically less than about 10,000,000:1, preferably less than about 1,000,000:1, and more preferably less than about 500,000:1.

The contacting time of the reagents and catalyst in a batch reactor can be any duration, provided that the desired olefin metathesis products are obtained. Generally, the contacting time in a reactor is greater than about 5 minutes, and preferably greater than about 10 minutes. Generally, the contacting time in a reactor is less than about 25 hours, preferably less than about 15 hours, and more preferably less than about 10 hours.

In a preferred embodiment, the reactants (for example, metathesis catalyst; feed materials; optional alkene, optional alcohol, optional water, etc.) are combined in a reaction vessel at a temperature of 20 to 300° C. (preferably 20 to 200° C., preferably 30 to 100° C., preferably 40 to 60° C.) and an alkene (such as ethylene) at a pressure of 0.1 to 1000 psi (0.7 kPa to 6.9 MPa), preferably 20 to 400 psi (0.14 MPa to 2.8 MPa), preferably 50 to 250 psi (0.34 MPa to 1.7 MPa), if the alkene is present, for a residence time of 0.5 seconds to 48 hours (preferably 0.25 to 5 hours, preferably 30 minutes to 2 hours).

In certain embodiments, where the alkene is a gaseous olefin, the olefin pressure is greater than about 5 psig (34.5 kPa), preferably, greater than about 10 psig (68.9 kPa), and more preferably, greater than about 45 psig (310 kPa). When a diluent is used with the gaseous alkene, the aforementioned pressure ranges may also be suitably employed as the total pressure of olefin and diluent. Likewise, when a liquid alkene is employed and the process is conducted under an inert gaseous atmosphere, then the aforementioned pressure ranges may be suitably employed for the inert gas pressure.

In a preferred embodiment, from about 0.005 nmoles to about 500 nmoles, preferably from about 0.1 to about 250 nmoles, and most preferably from about 1 to about 50 nmoles of the metathesis catalyst are charged to the reactor per 3 mmoles of feed material (such as TAGs, biodiesel, fatty acids, fatty acid esters, and/or fatty acid alkyl esters or mixtures thereof, preferably fatty acid esters) charged.

In a preferred embodiment, the process is typically a solution process, although it may be a bulk or high pressure process. Homogeneous processes are preferred. (A homogeneous process is defined to be a process where at least 90 wt % of the product is soluble in the reaction media.) A bulk homogeneous process is particularly preferred. (A bulk process is defined to be a process where reactant concentration in all feeds to the reactor is 70 volume % or more.) Alternately, no solvent or diluent is present or added in the reaction medium, (except for the small amounts used as the carrier for the catalyst or other additives, or amounts typically found with the reactants, e.g., propane in propylene).

Suitable diluents/solvents for the process include non-coordinating, inert liquids. Examples include straight and branched-chain hydrocarbons such as isobutane, butane, pentane, isopentane, hexanes, isohexane, heptane, octane, dodecane, and mixtures thereof; cyclic and alicyclic hydrocarbons such as cyclohexane, cycloheptane, methylcyclohexane, methylcycloheptane, and mixtures thereof such as can be found commercially (Isopar™); perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable diluents/solvents also include aromatic hydrocarbons, such as toluene or xylenes, and chlorinated solvents, such as dichloromethane. In a preferred embodiment, the feed concentration for the process is 60 volume % solvent or less, preferably 40 volume % or less, preferably 20 volume % or less.

The process may be batch, semi-batch or continuous. As used herein, the term continuous means a system that operates without interruption or cessation. For example, a continuous process to produce a polymer would be one where the reactants are continually introduced into one or more reactors and polymer product is continually withdrawn.

Useful reaction vessels include reactors (including continuous stirred tank reactors, batch reactors, reactive extruder, pipe, or pump.

The processes may be conducted in either glass lined, stainless steel, or similar type reaction equipment. Useful reaction vessels include reactors (including continuous stirred tank reactors, batch reactors, reactive extruder, pipe, or pump, continuous flow fixed bed reactors, slurry reactors, fluidized bed reactors, and catalytic distillation reactors). The reaction zone may be fitted with one or more internal and/or external heat exchanger(s) in order to control undue temperature fluctuations, or to prevent "runaway" reaction temperatures.

If the process is conducted in a continuous flow reactor, then the weight hourly space velocity, given in units of grams feed material (preferably fatty acid ester and/or fatty acid alkyl ester) per gram catalyst per hour ($h^{-1}$), will determine the relative quantities of feed material to catalyst employed, as well as the residence time in the reactor of the unsaturated starting compound. In a flow reactor, the weight hourly space velocity of the unsaturated feed material (preferably fatty acid ester and/or fatty acid alkyl ester) is typically greater than about 0.04 g feed material (preferably fatty acid ester and/or fatty acid alkyl ester) per g catalyst per hour ($h^{-1}$), and preferably, greater than about 0.1 $h^{-1}$. In a flow reactor, the weight hourly space velocity of the feed material (preferably fatty acid ester and/or fatty acid alkyl ester) is typically less than about 100 $h^{-1}$, and preferably, less than about 20 $h^{-1}$.

In certain embodiments, reactions utilizing the catalytic complexes of the present invention can be run in a biphasic mixture of solvents, in an emulsion or suspension, or in a lipid vesicle or bilayer.

The feed material is typically provided as a liquid phase, preferably neat. In particular embodiments, the feed material is provided in a liquid phase, preferably neat; while the alkene is provided as a gas that is dissolved in the liquid phase. In certain embodiments, feed material is an unsaturated fatty acid ester or unsaturated fatty acid and is provided in a liquid phase, preferably neat; while the alkene is a gaseous alpha-olefin, such as for example, ethylene, which is dissolved in the liquid phase.

Generally, the feed material is an unsaturated fatty acid ester or unsaturated fatty acid and is provided as a liquid at the process temperature, and it is generally preferred to be used neat, that is, without a diluent or solvent. The use of a solvent usually increases recycle requirements and increases costs. Optionally, however, if desired, a solvent can be employed with the alkene and/or feed material. A solvent may be desirable, for instance, where liquid feed material and alkene are not entirely miscible, and both then can be solubilized in a suitable solvent.

In a preferred embodiment, the alkene and an unsaturated fatty acid ester or unsaturated fatty acid are co-metathesized to form first and second product olefins, preferably, a reduced chain first product alpha-olefin and a second product reduced chain terminal ester or acid-functionalized alpha-olefin. As a preferred example, the metathesis of methyloleate with ethylene will yield cross-metathesis products of 1-decene and methyl-9-decenoate. Both products are alpha-olefins; the decenoate also terminates in an ester moiety at the opposite end of the chain from the carbon-carbon double bond. In addition to the desired products, the methyloleate may self-metathesize to produce small amounts of 9-octadecene, a less desirable product, and dimethyl-9-octadecene-1,18-dioate, $CH_3OC(O)$ $(CH_2)_7CH=CH(CH_2)_7C(O)O$ $CH_3$, a second less desirable product.

In the process of this invention, the conversion of feed material (preferably fatty acid ester and/or fatty acid alkyl ester) can vary widely depending upon the specific reagent olefins, the specific catalyst, and specific process conditions employed. For the purpose of this invention, "conversion" is defined as the mole percentage of feed material that is converted or reacted to the cross-metathesis alpha-olefin products. Typically, the conversion of feed material (preferably fatty acid ester and/or fatty acid alkyl ester) is greater than about 50 mole %, preferably, greater than about 60 mole %, and more preferably, greater than about 70 mole %.

In the process of this invention, the yields of first product olefin and ester or acid-functionalized second product olefin can also vary depending upon the specific reagent olefins, catalyst, and process conditions employed. For the purposes of this invention "yield" will be defined as the mole percentage of cross-metathesis alpha-olefin product formed relative to the initial moles of feed material (such as fatty acid ester and/or fatty acid alkyl ester) in the feed. Typically, the yield of alpha-olefin will be greater than about 35 mole %, preferably, greater than about 50 mole %. Typically, the yield of ester or acid-functionalized alpha-olefin will be 30% or more, preferably 40% or more, preferably 45% or more, preferably 50% or more, preferably 55% or more, preferably 60% or more.

In a preferred embodiment, the yield for reactions (when converting TAGs as represented in the formula below), is defined as the moles of alpha olefin formed divided by (the moles of unsaturated $R^a$+moles of unsaturated $R^b$+moles of unsaturated $R^c$) introduced into the reactor is 30% or more, preferably 40% or more, preferably 45% or more, preferably 50% or more, preferably 55% or more, preferably 60% or more,

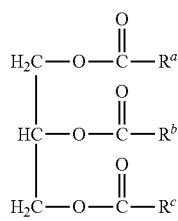

where $R^a$, $R^b$, and $R^c$ each, independently, represent a saturated or unsaturated hydrocarbon chain (preferably $R^a$, $R^b$, and $R^c$ each, independently, are a $C_{12}$ to $C_{28}$ alkyl or alkene, preferably $C_{16}$ to $C_{22}$ alkyl or alkene).

For the purposes of this invention, "productivity" is defined to be the amount in grams of linear alpha-olefin produced per mmol of catalyst introduced into the reactor, per hour. In a preferred embodiment, the productivity of the process is at least 200 g of linear alpha-olefin (such as decene-1) per mmol of catalyst per hour, preferably at least 5000 g/mmol/hour, preferably at least 10,000 g/mmol/hour, preferably at least 300,000 g/mmol/hour.

For the purposes of this invention, "selectivity" is a measure of conversion of alkene and feed material to the cross-metathesis alpha-olefin product, and is defined by the mole percentage of product olefin formed relative to the initial moles of alkene or feed material. In a preferred embodiment, the selectivity of the process is at least 20 wt % linear alpha-olefin, based upon the weight to the material exiting the reactor, preferably at least 25 wt %, preferably at least 30 wt %, preferably at least 35 wt %, preferably at least 40 wt %, preferably at least 45 wt %, preferably at least 50 wt %, preferably at least 60 wt %, preferably at least 70 wt %, preferably at least 80 wt %, preferably at least 85 wt %, preferably at least 90 wt %, preferably at least wt 95%.

For the purpose of this invention, "catalyst turnover number" (TON) is a measure of how active the catalyst compound is and is defined as the number of moles of cross-metathesis alpha-olefin product formed per mole of catalyst compound. In a preferred embodiment, the (TON), of the process is at least 5,000, preferably at least 10,000, preferably at least 50,000, preferably at least 100,000, preferably at least 1,000,000.

Feed Materials

Feed materials useful in metathesis processes described herein include feed oils, fatty acids, fatty acid esters, triacylglycerides, and biodiesel.

Feed Oils

The fatty acid rich material useful in the processes described herein can be derived from plant, animal, microbial, or other sources (feed oil). Preferred feed oils include vegetable oils such as corn, soy, rapeseed, canola, sunflower, palm and other oils that are readily available; however, any vegetable oil or animal fat can be employed. Raw or unrefined oil can be used in certain embodiments; however, filtered and refined oils are typically preferred. Use of degummed and filtered feedstock minimizes the potential for emulsification and blockage in the reactors. Feedstock with high water content can be dried before basic catalyst processing. Feedstock with high free fatty acid content can be passed through an esterification process to reduce the free fatty acid content before the process of esterification to convert fatty acid glycerides to monoalkyl esters. The reduction of free fatty acids and the conversion of fatty acid glycerides can also in the same processing step. Feedstock containing other organic compounds (such as hexane, heptane, isohexane, etc.) can typically be processed without significant modifications to the reactor. Other materials containing fatty acid glycerides or other fatty acid esters can also be employed, including phospholipids, lysophospholipids, and fatty acid wax esters. The fatty acid rich material useful in the processes described herein typically includes a mixture of fatty acids. For example, the fatty acid profiles of several potential feedstocks are shown in Table 1. The feed oil can also include a mixture of fatty acid glycerides from different sources. The free fatty acid content of useful vegetable oils is preferably about 0.1 wt % or less when employed in a basic homogeneous catalyst esterification reaction. Higher levels can be utilized as well, and levels up to about 3 wt %, or even as high as 15 wt % or more can typically be tolerated.

For purposes of this invention and the claims thereto the term "feed oil" refers to one or more vegetable or animal oils, such as canola oil, corn oil, soybean oil, beef tallow, tall oil, animal fats, waste oils/greases, rapeseed oil, algae oil, peanut oil, mustard oil, sunflower oil, tung oil, perilla oil, grapeseed oil, linseed oil, safflower oil, pumpkin oil, palm oil, Jathropa oil, high-oleic soybean oil, high-oleic safflower oil, high-oleic sunflower oil, mixtures of animal and/or vegetable fats and oils, castor bean oil, dehydrated castor bean oil, cucumber oil, poppyseed oil, flaxseed oil, lesquerella oil, walnut oil, cottonseed oil, meadowfoam, tuna oil, and sesame oils.

Vegetable oils useful herein preferably contain at least one site of unsaturation and include, but are not limited to, canola, soybean, palm, peanut, mustard, sunflower, tung, tall, perilla, grapeseed, rapeseed, linseed, safflower, pumpkin corn and other oils extracted from plant seeds.

In a preferred embodiment, a combination of oils is used herein. Preferred combinations include two (three or four) or more of tall oil, palm oil, tallow, waste grease, rapeseed oil, canola oil, soy oil and algae oil. Alternate useful combinations include two (three or four) or more of soy oil, canola oil, rapeseed oil, algae oil, and tallow.

In certain embodiments, processed oils, such as blown oils, are the source of fatty acids useful herein. While vegetable oils are preferred sources of fatty acids for practicing disclosed embodiments of the present process, fatty acids also are available from animal fats including, without limitation, lard and fish oils, such as sardine oil and herring oil, and the like. As noted above, in certain embodiments, a desired fatty acid or fatty acid precursor is produced by a plant or animal found in nature. However, particular fatty acids or fatty acid precursors are advantageously available from genetically modified organisms, such as a genetically modified plants, particularly genetically modified algae. Such genetically modified organisms are designed to produce a desired fatty acid or fatty acid precursor biosynthetically or to produce increased amounts of such compounds.

TABLE 1

Fatty Acid Profile of Several Typical Feed Oils

| Fatty Acid | Palm Oil | Soy Oil | High Oleic Rapeseed | Yellow Grease |
|---|---|---|---|---|
|  | 0 wt % | 0 wt % | 0 wt % | 0 wt % |
| C6:0 | 0 wt % | 0 wt % | 0 wt % | 0 wt % |
| C8:0 | 0 wt % | 0 wt % | 0 wt % | 0 wt % |
| C10:0 | 0 wt % | 0 wt % | 0 wt % | 0 wt % |
| C12:0 | 0 wt % | 0 wt % | 0 wt % | 0 wt % |
| C14:0 | 1 wt % | 0 wt % | 0 wt % | 2 wt % |
| C16:0 | 44 wt % | 7 wt % | 4 wt % | 23 wt % |
| C18:0 | 5 wt % | 5 wt % | 1 wt % | 13 wt % |
| C18:1 | 39 wt % | 28 wt % | 60 wt % | 44 wt % |
| C18:2 | 10 wt % | 53 wt % | 21 wt % | 7 wt % |
| C18:3 | 0 wt % | 0 wt % | 13 wt % | 1 wt % |
| C20:0 | 0 wt % | 0 wt % | 0 wt % | 0 wt % |
| C22:1 | 0 wt % | 0 wt % | 0 wt % | 0 wt % |
| Misc. | 1 wt % | 8 wt % | 0 wt % | 9 wt % |

Fatty Acids and Fatty Acid Esters

Fatty acids are carboxylic acids with a saturated or unsaturated aliphatic tails that are found naturally in many different fats and oils. Any unsaturated fatty acid can be suitably employed in the process of this invention, provided that the unsaturated fatty acid can be metathesized in the manner disclosed herein. An unsaturated fatty acid comprises a long carbon chain containing at least one carbon-carbon double bond and terminating in a carboxylic acid group. Typically, the unsaturated fatty acid will contain greater than about 8 carbon atoms, preferably, greater than about 10 carbon atoms, and more preferably, greater than about 12 carbon atoms. Typically, the unsaturated fatty acid will contain less than about 50 carbon atoms, preferably, less than about 35 carbon atoms, and more preferably, less than about 25 carbon atoms. At least one carbon-carbon double bond is present along the carbon chain, this double bond usually occurring about the middle of the chain, but not necessarily. The carbon-carbon double bond may also occur at any other internal location along the chain. A terminal carbon-carbon double bond, at the opposite end of the carbon chain relative to the terminal carboxylic acid group, is also suitably employed, although terminal carbon-carbon double bonds occur less commonly in fatty acids. Unsaturated fatty acids containing the terminal carboxylic acid functionality and two or more carbon-carbon double bonds may also be suitably employed in the process of this invention.

Because metathesis can occur at any of the carbon-carbon double bonds, a fatty acid having more than one double bond may produce a variety of metathesis products. The unsaturated fatty acid may be straight or branched and substituted along the fatty acid chain with one or more substituents, provided that the one or more substituents are substantially inert with respect to the metathesis process. Non-limiting examples of suitable substituents include alkyl moieties, preferably $C_{1-10}$ alkyl moieties, including, for example, methyl, ethyl, propyl, butyl, and the like; cycloalkyl moieties, preferably, $C_{4-8}$ cycloalkyl moieties, including for example, cyclopentyl and cyclohexyl; monocyclic aromatic moieties, preferably, $C_6$ aromatic moieties, that is, phenyl; arylalkyl moieties, preferably, $C_{7-16}$ arylalkyl moieties, including, for example, benzyl; and alkylaryl moieties, preferably, $C_{7-16}$ alkylaryl moieties, including, for example, tolyl, ethylphenyl, xylyl, and the like; as well as hydroxyl, ether, keto, aldehyde, and halide, preferably, chloro and bromo, functionalities.

Non-limiting examples of suitable unsaturated fatty acids include 3-hexenoic (hydrosorbic), trans-2-heptenoic, 2-octenoic, 2-nonenoic, cis and trans-4-decenoic, 9-decenoic (caproleic), 10-undecenoic (undecylinic), trans-3-dodecenoic (linderic), tridecenoic, cis-9-tetradeceonic (myristoleic), pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (gadoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), and like acids. Oleic acid is most preferred. Unsaturated fatty acids can be obtained commercially or synthesized by saponifying fatty acid esters, this method being known to those skilled in the art.

Fatty acid esters are formed by condensation of a fatty acid and an alcohol. Fatty acid alkyl esters are fatty acids where the hydrogen of the —OH of the acid group is replaced by a hydrocarbyl group, typically a $C_1$ to $C_{30}$ alkyl group, preferably a $C_1$ to $C_{20}$ alkyl.

Fatty acid alkyl esters are fatty acids where the hydrogen of the —OH of the acid group is replaced by an alkyl group. Fatty acid alkyl esters useful herein are typically represented by the formula: R^—C(O)—O—R*, where R^ is a $C_1$ to $C_{100}$ hydrocarbyl group, preferably a $C_6$ to $C_{22}$ group, preferably a $C_6$ to $C_{14}$ 1-alkene group, and R* is an alkyl group, preferably a $C_1$ to $C_{20}$ alkyl group, preferably methyl, ethyl, butyl, pentyl and hexyl. Preferred fatty acid alkyl esters useful herein are typically represented by the formula: $R\hat{}$—$CH_2$=$CH_2$—$R\hat{}$—C(O)—O—R*, where each $R\hat{}$ is, independently a $C_1$ to $C_{100}$ alkyl group, preferably a $C_6$ to $C_{20}$, preferably a $C_8$ to $C_{14}$ alkyl group, preferably a $C_9$ group and R* is an alkyl group, preferably a $C_1$ to $C_{20}$ alkyl group, preferably methyl, ethyl, butyl, pentyl and hexyl. Particularly preferred fatty acid alkyl esters useful herein are represented by the formula:

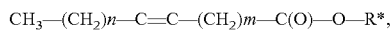

$CH_3$—$(CH_2)n$—C=C—$(CH_2)m$—C(O)—O—R*, where and R* is an alkyl group, preferably a $C_1$ to $C_{20}$ alkyl group, preferably methyl, ethyl, butyl pentyl and hexyl, m and n are, independently 1, 2, 3, 4, 5, 6, 7, 8, 9, 10, 11, 12, 13, 14, 15, or 16, preferably 5, 7, 9, or 11, preferably 7.

Fatty acid methyl esters are fatty acids where the hydrogen of the —OH of the acid group is replaced by methyl group. Fatty acid methyl esters useful herein are typically represented by the formula: $R\hat{}$—C(O)—O—$CH_3$, where $R\hat{}$ is a $C_1$ to $C_{100}$ hydrocarbyl group, preferably a $C_6$ to $C_{22}$ group, preferably a $C_6$ to $C_{14}$ 1-alkene group. Preferred fatty acid methyl esters useful herein are typically represented by the formula: $R\hat{}$—$CH_2$=$CH_2$—$R\hat{}$—C(O)—O—$CH_3$, where each $R\hat{}$ is, independently a $C_1$ to $C_{100}$ alkyl group, preferably a $C_6$ to $C_{20}$, preferably a $C_8$ to $C_{14}$ alkyl group, preferably a $C_9$ group. Particularly preferred fatty acid methyl esters useful herein are represented by the formula: $CH_3$—$(CH_2)n$—C=C—$(CH_2)m$—C(O)—O—$CH_3$, where m and n are, independently 1, 2, 3, 4, 5, 6, 7, 8, 9, 10, 11, 12, 13, 14, 15, or 16, preferably 5, 7, 9, or 11, preferably 7.

Preferred fatty acid methyl esters include methyl palmitoleate, methyl oleate, methyl gadoleate, methyl erucate, methyl linoleate, methyl linolenate, methyl soyate, and mixtures of methyl esters derived from soybean oil, beef tallow, tall oil, animal fats, waste oils/greases, rapeseed oil, algae oil, Canola oil, palm oil, Jathropa oil, high-oleic soybean oil (e.g., 75 mole % or more, preferably 85 mole % or more, preferably 90 mole % or more), high-oleic safflower oil (e.g., 75 mole % or more, preferably 85 mole % or more, preferably 90 mole % or more), high-oleic sunflower oil (e.g., 75 mole % or more, preferably 85 mole % or more, preferably 90 mole % or more), and other plant or animal derived sources containing fatty acids.

Alcohol (Also Referred to as Alkanols)

Fatty acid esters are formed by condensation of a fatty acid and an alcohol. The alcohol used herein can be any monohydric, dihydric, or polyhydric alcohol that is capable of condensing with the feed material (such as the unsaturated fatty acid) to form the corresponding unsaturated ester (such as the fatty acid ester). Typically, the alcohol contains at least one carbon atom. Typically, the alcohol contains less than about 20 carbon atoms, preferably, less than about 12 carbon atoms, and more preferably, less than about 8 carbon atoms. The carbon atoms may be arranged in a straight-chain or branched structure, and may be substituted with a variety of substituents, such as those previously disclosed hereinabove in connection with the fatty acid, including the aforementioned alkyl, cycloalkyl, monocyclic aromatic, arylalkyl, alkylaryl, hydroxyl, halogen, ether, ester, aldehyde and keto substituents. Preferably, the alcohol is a straight-chain or a branched $C_{1-12}$ alkanol. A preferred alcohol is the trihydric alcohol glycerol, the fatty acid esters of which are known as "glycerides." Other preferred alcohols include methanol and ethanol.

Preferably, the alcohol employed in the esterification and/or transesterification reactions is preferably a low molecular weight monohydric alcohol such as methanol, ethanol, 1-propanol, 2-propanol, 1-butanol, 2-butanol, or t-butanol. The alcohol is preferably anhydrous; however, a small amount of water in the alcohol may be present (e.g., less than about 2 wt %, preferably less than about 1 wt %, and most preferably less than about 0.5 wt %; however, in certain embodiments, higher amounts can be tolerated). Acid esterification reactions are more tolerant of the presence of small amounts of water in the alcohol than are basic transesterification reactions. While specific monohydric alcohols are discussed herein with reference to certain embodiments and examples, the preferred embodiments are not limited to such specific monohydric alcohols. Other suitable monohydric alcohols can also be employed in the preferred embodiments.

Preferred sources of fatty acid esters for use herein include TAGs and biodiesel sources.

Biodiesel

Biodiesel is a mono-alkyl ester derived from the processing of vegetable oils and alcohols. The processing is typically carried out by an esterification reaction mechanism, and typically is performed in an excess of alcohol to maximize conversion. Esterification can refer to direct esterification, such as between a free fatty acid and an alcohol, as well as transesterification, such as between an ester and an alcohol. While vegetable oil and alcohols are commonly employed as reactants in esterification reactions, a fatty acid source such as free fatty acids, soaps, esters, glycerides (mono-, di- tri-), phospholipids, lysophospholipids, or amides and a monohydric alcohol source, such as an alcohol or an ester, can be esterified. In addition, various combinations of these reagents can be employed in an esterification reaction.

Alkyl oleates and alkyl erucates are fatty acid esters that are often major components in biodiesel produced by the transesterification of alcohol and vegetable oils (preferably the alkyls are a $C_1$ to $C_{30}$ alkyl group, alternately a $C_1$ to $C_{20}$ alkyl group). Biodiesel compositions that are particularly useful in this invention are those which have high concentrations of alkyl oleate and alkyl erucate esters. These fatty acid esters preferably have one site of unsaturation such that cross-metathesis with ethylene yields 1-decene as the coproduct. Biodiesel compositions that are particularly useful are those produced from vegetable oils such as canola, rapeseed oil, palm oil, and other high oleate oil, high erucate oils. Particularly preferred vegetable oils include those having at least 50% (on a molar basis) combined oleic and erucic fatty acid chains of all fatty acid chains, preferably 60%, preferably 70%, preferably 80%, preferably 90%.

In another embodiment, useful fatty acid ester containing mixtures include those having at least 50% (on a molar basis) alkyl oleate fatty acid esters, preferably 60% of alkyl oleate fatty acid esters, preferably 70% of alkyl oleate fatty acid esters, preferably 80% of alkyl oleate fatty acid esters, preferably 90% of alkyl oleate fatty acid esters.

In another embodiment, useful fatty acid ester containing mixtures include those having at least 50% (on a molar basis) alkyl erucate fatty acid esters, preferably 60% of alkyl erucate fatty acid esters, preferably 70% of alkyl erucate fatty acid esters, preferably 80% of alkyl erucate fatty acid esters, preferably 90% of alkyl erucate fatty acid esters.

In another embodiment, useful fatty acid ester containing mixtures include those having at least 50% (on a molar basis) combined oleic and erucic fatty acid esters of all fatty acid ester chains, preferably 60%, preferably 70%, preferably 80%, preferably 90%.

Triacylglycerides (TAGs)

Triacylglycerides (TAGs), also called triglycerides, are a naturally occurring ester of three fatty acids and glycerol that is the chief constituent of natural fats and oils. The three fatty acids can be all different, all the same, or only two the same, they can be saturated or unsaturated fatty acids, and the saturated fatty acids may have one or multiple unsaturations. Chain lengths of the fatty acids in naturally occurring triacylglycerides can be of varying lengths but 16, 18, and 20 carbons are the most common. Natural fatty acids found in plants and animals are typically composed only of even numbers of carbon atoms due to the way they are bio-synthesized. Most natural fats contain a complex mixture of individual triglycerides and because of this, they melt over a broad range of temperatures.

Vegetable oils include triglycerides and neutral fats, such as triacylglycerides, the main energy storage form of fat in animals and plants. These typically have the chemical structure:

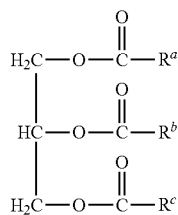

where $R^a$, $R^b$, and $R^c$ each, independently, represent a saturated or non-saturated hydrocarbon chain (preferably $R^a$, $R^b$, and $R^c$ each, independently, are a $C_{12}$ to $C_{28}$ alkyl or alkene, preferably $C_{16}$ to $C_{22}$ alkyl or alkene). Different vegetable oils have different fatty acid profiles, with the same or different fatty acids occurring on a single glycerol. For example, an oil can have linoleic, oleic, and stearic acids attached to the same glycerol, with each of $R^a$, $R^b$, and $R^c$ representing one of these three fatty acids. In another example, there can be two oleic acids and one stearic acid attached to the same glycerol, each of $R^a$, $R^b$, and $R^c$ representing one of these fatty acids. A particularly useful triglyceride consists of three fatty acids (e.g., saturated fatty acids of general structure of $CH_3(CH_2)_n$ COOH, wherein n is typically an integer of from 4 to 28 or higher) attached to a glycerol ($C_3H_5(OH)_3$) backbone by ester linkages.

Transesterification/Esterification Reactions

In the esterification process, vegetable oils and short chain alcohols are reacted to form mono-alkyl esters of the fatty acid and glycerol (also referred to as glycerin). When the alcohol used is methanol ($CH_3OH$), a methyl ester is created with the general form $CH_3(CH_2)_nCOOCH_3$ for saturated fatty acids. Typically, but not always, the length of the carbon backbone chain is from 12 to 24 carbon atoms.

The esterification process can be catalyzed or non-catalyzed. Catalyzed processes are categorized into chemical and enzyme based processes. Chemical catalytic methods can employ acid and/or base catalyst mechanisms. The catalysts can be homogeneous and/or heterogeneous catalysts. Homogeneous catalysts are typically liquid phase mixtures, whereas heterogeneous catalysts are solid phase catalysts mixed with the liquid phase reactants, oils and alcohols.

In processes herein, the conversion of TAGs to fatty acid alkyl esters ("FAAE") through transesterification of the TAG typically involves forming a reactant stream, which includes TAG (e.g., at least about 75 wt %), alkanol (e.g., about 5 to 20 wt %), a transesterification catalyst (e.g., about 0.05 to 1 wt %), and optionally, glycerol (typically up to about 10 wt %). Suitable alkanols may include $C_1$-$C_6$ alkanols and commonly may include methanol, ethanol, or mixtures thereof. Suitable transesterification catalysts may include alkali metal alkoxides having from 1 to 6 carbon atoms and commonly may include alkali metal methoxide, such as sodium methoxide and/or potassium methoxide. The basic catalyst is desirably selected such that the alkali metal alkoxide may suitably contain an alkoxide group which is the counterpart of the alkanol employed in the reaction stream (e.g., a combination of methanol and an alkali metal methoxide such as sodium methoxide and/or potassium methoxide). The reactant stream may suitably include about 0.05 to 0.3 wt % sodium methoxide, at least about 75 wt % triacylglyceride, about 1 to 7 wt % glycerol, and at least about 10 wt % methanol. In some embodiments, the reactant stream may desirably include about 0.05 to 0.25 wt % sodium methoxide, at least about 75 wt % triacylglyceride, about 2 to 5 wt % glycerol, and about 10 to 15 wt % methanol.

The rate and extent of reaction for esterification of the fatty acid glycerides or other fatty acid derivates with monohydric alcohol in the presence of a catalyst depends upon factors including but not limited to the concentration of the reagents, the concentration and type of catalyst, and the temperature and pressure conditions, and time of reaction. The reaction generally proceeds at temperatures above about 50° C., preferably at temperatures above 65° C.; however, the catalyst selected or the amount of catalyst employed can affect this temperature to some extent. Higher temperatures generally result in faster reaction rates. However, the use of very high temperatures, such as those in excess of about 300° C., or even those in excess of 250° C., can lead to increased generation of side products, which can be undesirable as their presence can increase downstream purification costs. Higher temperatures can be advantageously employed; however, e.g., in situations where the side products do not present an issue.

The reaction temperature can be achieved by preheating one or more of the feed materials or by heating a mixture of the feed materials. Heating can be achieved using apparatus known in the art, e.g., heat exchangers, jacketed vessels, submerged coils, and the like. While specific temperatures and methods of obtaining the specific temperatures are discussed herein with reference to certain embodiments and examples, the preferred embodiments are not limited to such specific temperatures and methods of obtaining the specific temperatures. Other temperatures and methods of obtaining temperatures can also be employed in the preferred embodiments.

The amount of alcohol employed in the reaction is preferably in excess of the amount of fatty acid present on a molar basis. The fatty acid can be free or combined, such as to alcohol, glycol, or glycerol, with up to three fatty acid moieties being attached to a glycerol. Additional amounts of alcohol above stoichiometric provide the advantage of assisting in driving the equilibrium of the reaction to produce more of the fatty acid ester product. However, greater excesses of alcohol can result in greater processing costs and larger capital investment for the larger volumes of reagents employed in the process, as well as greater energy costs associated with recovering, purifying, and recycling this excess alcohol. Accordingly, it is generally preferred to employ an amount of alcohol yielding a molar ratio of alcohol to fatty acid of from about 15:1 to about 1:1 (stoichiometric), and more preferably from about 4:1 to about 2:1; however the process can operate over a much wider range of alcohol to fatty acid ratios, with nonreacted materials subjected to recycling or other processing steps. Generally, lower relative levels of alcohol to fatty acid result in decreased yield and higher relative levels of alcohol levels to fatty acid result in increased capital and operating expense. Some instances of operation at ratios of alcohol to fatty acid over a wider range include when first starting up the process or shutting down the process, when balancing the throughput of the reactor to other processing steps or other processing facilities, such as one that produces alcohol or utilizes a side stream, or when process upsets occur. When a molar ratio of 2:1 methanol to fatty acid is employed and a sodium hydroxide concentration of about 0.5 wt % of the total reaction mixture is employed, the ratio of sodium hydroxide to methanol is about 2 wt % entering the reactor and about 4 wt % at the exit because about half of the alcohol is consumed in the esterification reaction.

Similarly, higher amounts of catalyst generally result in faster reactions. However, higher amounts of catalyst can lead to higher downstream separation costs and a different profile of side reaction products. The amount of homogeneous catalyst is preferably from about 0.2 wt % to about 1.0 wt % of the reaction mixture when the catalyst is sodium hydroxide; at typical concentration of 0.5 wt % when a 2:1 molar ratio of methanol to fatty acid is used; however, in certain embodiments, higher or lower amounts can be employed. The amount of catalyst employed can also vary depending upon the nature of the catalyst, feed materials, operating conditions, and other factors. Specifically, the temperature, pressure, free fatty acid content of the feed, and degree of mixing can change the amount of catalyst preferably employed. While specific catalyst amounts are discussed herein with reference to certain embodiments and examples, the preferred embodiments are not limited to such specific catalyst amounts. Other suitable catalyst amounts can also be employed in the preferred embodiments.

The esterification reaction can be performed batchwise, such as in a stirred tank, or it can be performed continuously, such as in a continuous stirred tank reactor (CSTR) or a plug flow reactor (PFR). When operated in continuous mode, a series of continuous reactors (including CSTRs, PFRs, or combinations thereof) can advantageously operate in series. Alternatively, batch reactors can be arranged in parallel and/or series.

When the reactor is operated in a continuous fashion, one or more of the feed materials is preferably metered into the process. Various techniques for metering can be employed (e.g., metering pumps, positive displacement pumps, control valves, flow meters, and the like). While specific types of reactors are discussed herein with reference to certain embodiments and examples, the preferred embodiments are not limited to such specific reactors. Other suitable types of reactors can also be employed in the preferred embodiments.

As described above, biodiesel refers to a transesterified vegetable oil or animal fat based diesel fuel containing long-chain alkyl (typically methyl, propyl, or ethyl) esters. Biodiesel is typically made by chemically reacting lipids (such as vegetable oil) with an alcohol. Biodiesel, TAG's and derivatives thereof may be used in the processes described herein. Likewise, preferred fatty acid methyl esters useful herein may be obtained by reacting canola oil, corn oil, soybean oil, beef tallow, tall oil, animal fats, waste oils/greases, rapeseed oil, algae oil, Canola oil, palm oil, Jathropa oil, high-oleic soybean oil, high-oleic safflower oil, high-oleic sunflower oil, or mixtures of animal and/or vegetable fats, and oils with one or more alcohols (as described above), preferably methanol.

Isomerization

In another embodiment, the feed material is first isomerized, then combined with a metathesis catalyst as described herein. For example, the processes disclosed herein may comprise providing a feed material (typically a fatty acid or fatty acid derivative), isomerizing a site of unsaturation in the feed material (typically a fatty acid or fatty acid derivative) to produce an isomerized feed material (typically a fatty acid or fatty acid derivative), and then contacting the isomerized material with an alkene in the presence of a metathesis catalyst. The isomerized material can be produced by isomerization with or without subsequent esterification or transesterification. Isomerization can be catalyzed by known biochemical or chemical techniques. For example, an isomerase enzyme, such as a linoleate isomerase, can be used to isomerize linoleic acid from the cis 9, cis 12 isomer to the cis 9, trans 11 isomer. This isomerization process is stereospecific, however, nonstereospecific processes can be used because both cis and trans isomers are suitable for metathesis. For example, an alternative process employs a chemical isomerization catalyst, such as an acidic or basic catalyst, can be used to isomerize an unsaturated feed material (typically a fatty acid or fatty acid derivative) having a site of unsaturation at one location in the molecule into an isomerized, feed material (typically a fatty acid or fatty acid derivative) having a site of unsaturation at a different location in the molecule. Metal or organometallic catalysts also can be used to isomerize an unsaturated feed material (typically a fatty acid or fatty acid derivative). For example, nickel catalysts are known to catalyze positional isomerization of unsaturated sites in fatty acid derivatives. Similarly, esterification, transesterification, reduction, oxidation, and/or other modifications of the starting compound or products, such as a fatty acid or fatty acid derivative, can be catalyzed by biochemical or chemical techniques. For example, a fatty acid or fatty acid derivative can be modified by a lipase, esterase, reductase or other enzyme before or after isomerization. In another embodiment, the isomerization described above may be practiced with any triacylglycerides, biodiesel, fatty acids, fatty acid esters, and/or fatty acid alkyl esters described herein, typically before contacting with the metathesis catalyst.

Alkenes

Besides the feed materials, the metathesis process of this invention may require an alkene as a reactant. The term "alkene" shall imply an organic compound containing at least one carbon-carbon double bond and typically having less than about 10 carbon atoms. The alkene may have one carbon-carbon unsaturated bond, or alternatively, two or more carbon-carbon unsaturated bonds. Since the metathesis reaction can occur at any double bond, alkenes having more than one double bond will produce more metathesis products. Accordingly, in some embodiments, it is preferred to employ an alkene having only one carbon-carbon double bond. The double bond may be, without limitation, a terminal double bond or an internal double bond. The alkene may also be substituted at any position along the carbon chain with one or more substituents, provided that the one or more substituents are essentially inert with respect to the metathesis process. Suitable substituents include, without limitation, alkyl, preferably, $C_{1-6}$ alkyl; cycloalkyl, preferably, $C_{3-6}$ cycloalkyl; as well as hydroxy, ether, keto, aldehyde, and halogen functionalities. Non-limiting examples of suitable alkenes include ethylene, propylene, butene, butadiene, pentene, hexene, the various isomers thereof, as well as higher homologues thereof. Preferably, the alkene is a $C_{2-8}$ alkene. More preferably, the alkene is a $C_{2-6}$ alkene, even more preferably, a $C_{2-4}$ alkene, and most preferably, ethylene.

Useful alkenes include those represented by the formula: $R^*-HC=CH-R^*$, wherein each $R^*$ is independently, hydrogen or a $C_1$ to $C_{20}$ hydrocarbyl, preferably hydrogen or a $C_1$ to $C_6$ hydrocarbyl, preferably hydrogen, methyl, ethyl, propyl or butyl, more preferably $R^*$ is hydrogen. In a preferred embodiment, both $R^*$ are the same, preferably both $R^*$ are hydrogen.

Ethylene, propylene, butene, pentene, hexene, octane, nonene and decene (preferably ethylene) are alkenes useful herein.

For purposes of this invention and the claims thereto, the term lower olefin means an alkene represented by the formula: R*-HC=CH—R*, wherein each R* is independently, hydrogen or a $C_1$ to $C_6$ hydrocarbyl, preferably hydrogen or a $C_1$ to $C_3$ hydrocarbyl, preferably hydrogen, methyl, ethyl, propyl, or butyl, more preferably R* is hydrogen. In a preferred embodiment, both R* are the same, preferably both R* are hydrogen. Ethylene, propylene, butene, pentene, hexene, and octene (preferably ethylene) are lower olefins useful herein.

Alpha-Olefin Products of the Metathesis Reaction

In a preferred embodiment, the processes described herein produce a linear alpha olefin. The alpha-olefin, preferably linear alpha-olefin, produced herein contains at least one more carbon than the alkene used in the reaction to make the alpha-olefin.

In another embodiment, the processes described herein produce a blend of an alpha olefin and an ester-functionalized alpha olefin. Generally a mixture of non-ester-containing alpha olefins will be produced due to the presence of mono-, di-, and tri-unsubstituted fatty acid chains. The major alpha olefin products are expected to be 1-decene, 1-heptene, and 1-butene. The major ester-containing alpha olefin product is methyl dec-9-enoate.

In a preferred embodiment, the alpha olefin produced herein is 1-decene. Typically the 1-decene is produced with an ester.

In a preferred embodiment, the major alpha olefin produced herein is 1-decene. Typically the 1-decene is produced with an ester.

In a preferred embodiment, ethylene and methyl oleate are combined with the metathesis catalysts described herein (such as 2-(i-propoxy)-5-(N,N-dimethylaminosulfonyl)phenylmethylene(1-cyclohexylmethyl-3-(2,6-diisopropylphenyl)-4,5-dihydro-1H-imidazole) ruthenium (II) chloride, (1-mesityl-3-methyl-2H-4,5-dihydroimidazol-2-ylidene) (tricyclohexylphosphine)-3-phenyl-1H-inden-1-ylidene ruthenium (II) dichloride, and mixtures thereof) to produce 1-decene and methyl dec-9-enoate.

Separation of the 1-olefin (such as the 1-decene) from the ester may be by means typically known in the art such as distillation or filtration.

The linear alpha-olefin (such as 1-decene or a mixture of $C_8$, $C_{10}$, $C_{12}$ linear alpha olefins) is then separated from any esters present and preferably used to make poly-alpha-olefins (PAOs). Specifically, PAOs may be produced by the polymerization of olefin feed in the presence of a catalyst such as $AlCl_3$, $BF_3$, or $BF_3$ complexes. Processes for the production of PAOs are disclosed, for example, in the following patents: U.S. Pat. Nos. 3,149,178; 3,382,291; 3,742,082; 3,769,363; 3,780,128; 4,172,855; and 4,956,122; which are fully incorporated by reference. PAOs are also discussed in: Will, J. G. *Lubrication Fundamentals*, Marcel Dekker New York, 1980. Certain high viscosity index PAO's may also be conveniently made by the polymerization of an alpha-olefin in the presence of a polymerization catalyst such as Friedel-Crafts catalysts. These include, for example, aluminum trichloride, boron trifluoride, aluminum trichloride, or boron trifluoride promoted with water, with alcohols such as ethanol, propanol, or butanol, with carboxylic acids, or with esters such as ethyl acetate or ethyl propionate or ether such as diethyl ether, diisopropyl ether, etc., see for example, the methods disclosed by U.S. Pat. Nos. 4,149,178; 3,382,291; 3,742,082; 3,769,363 (Brennan); U.S. Pat. Nos. 3,876,720; 4,239,930; 4,367,352; 4,413,156; 4,434,408; 4,910,355; 4,956,122; 5,068,487; 4,827,073; 4,827,064; 4,967,032; 4,926,004; and 4,914,254. PAO's can also be made using various metallocene catalyst systems. Examples include U.S. Pat. No. 6,706,828; WO 96/23751; EP 0 613 873; U.S. Pat. Nos. 5,688,887; 6,043,401; WO 03/020856; U.S. Pat. No. 6,548,724; 5,087,788; 6,414,090; 6,414,091; 4,704,491; 6,133,209; and 6,713,438.

PAOs are often used as additives and base stocks for lubricants, among other things. Additional information on the use of PAO's in the formulations of full synthetic, semi-synthetic or part synthetic lubricant or functional fluids can be found in "Synthetic Lubricants and High-Performance Functional Fluids", $2^{nd}$ Ed., L. Rudnick et al., Marcel Dekker, Inc., N.Y. (1999). Additional information on additives used in product formulation can be found in "Lubricants and Lubrications", Ed. By T. Mang and W. Dresel, by Wiley-VCH GmbH, Weinheim 2001.

In another embodiment, this invention relates to:

1. An asymmetrically substituted NHC metathesis catalyst compound represented by the formula:

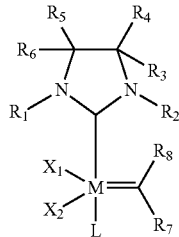

where:

M is a Group 8 metal; preferably Ru or Os, preferably Ru;

$X_1$ and $X_2$ are, independently, any anionic ligand (preferably halogen, an alkoxide or an alkyl sulfonate), or $X_1$ and $X_2$ may be joined to form a dianionic group and may form a single ring of up to 30 non-hydrogen atoms or a multinuclear ring system of up to 30 non-hydrogen atoms;

L is a heteroatom or heteroatom-containing ligand; preferably the heteroatom is N, O, P, or S; preferably P, optionally L may be joined to $R_7$ and/or $R_8$, preferably L is $L^*(R)_{q-1}$ when L is not bound to $R_7$ or $R_8$ or L is $L^*(R)_{q-2}$ when L is bound to $R_7$ or $R_8$, where q is 1, 2, 3, or 4 depending on the valence of $L^*$ (which may be 2, 3, 4, or 5) and $L^*$ is N, O, P, or S, (preferably P) and R is as defined for $R_3$;

and $R_1$, $R_2$, $R_3$, $R_4$, $R_5$, $R_6$, $R_7$, and $R_8$ are, independently, hydrogen or a $C_1$ to $C_{30}$ substituted or unsubstituted hydrocarbyl;

wherein any two adjacent R groups may form a single ring of up to 8 non-hydrogen atoms or a multinuclear ring system of up to 30 non-hydrogen atoms; and wherein $R_1$ and $R_2$ are dissimilar to each other.

2. The catalyst compound of paragraph 1, wherein M is ruthenium.

3. The catalyst compound of paragraph 1 or 2, wherein when $R_7$ and $R_8$ form an unsubstituted phenyl group and $R_1$ is mesityl, then $R_2$ is not methyl or ethyl, preferably $R_2$ is hydrogen or $C_1$ to $C_{30}$ substituted hydrocarbyl, or a $C_3$ to $C_{30}$ unsubstituted hydrocarbyl (preferably a $C_4$ to $C_{30}$ unsubstituted hydrocarbyl, preferably a $C_5$ to $C_{30}$ unsubstituted hydrocarbyl, preferably a $C_6$ to $C_{30}$ unsubstituted hydrocarbyl).

4. The catalyst compound of any of paragraphs 1 to 3, wherein $X_1$ and $X_2$ are Cl.

5. The catalyst compound of any of paragraphs 1 to 4, wherein the heteroatom in L is N, O, or P.
6. The catalyst compound of any of paragraphs 1 to 5, wherein $R_1$, $R_2$, $R_7$, and $R_8$ are, independently, $C_1$ to $C_{30}$ hydrocarbyl.
7. The catalyst compound of any of paragraphs 1 to 6, wherein $R_3$, $R_4$, $R_5$, and $R_6$ are, independently, hydrogen.
8. The catalyst compound of any of paragraphs 1 to 7, wherein $R_1$ is an aromatic hydrocarbyl or substituted hydrocarbyl and $R_2$ is an aliphatic hydrocarbyl or substituted hydrocarbyl, (preferably $R_1$ is a substituted or unsubstituted $C_6$ to $C_{30}$ aryl, and $R_2$ is a $C_1$ to $C_{30}$ substituted or unsubstituted alkyl, preferably $C_3$ to $C_{30}$ substituted or unsubstituted alkyl, preferably $C_4$ to $C_{30}$ substituted or unsubstituted alkyl, $C_5$ to $C_{30}$ substituted or unsubstituted alkyl, $C_6$ to $C_{30}$ substituted or unsubstituted alkyl).
9. The catalyst compound of paragraph 1, wherein the metathesis catalyst compound comprises one or more of: 2-(i-propoxy)-5-(N,N-dimethylaminosulfonyl)phenylmethylene(1-cyclohexylmethyl-3-(2,6-diisopropylphenyl)-4,5-dihydro-1H-imidazole) ruthenium (II) chloride, (1-mesityl-3-methyl-2H-4,5-dihydroimidazol-2-ylidene) (tricyclohexylphosphine)-3-phenyl-1H-inden-1-ylidene ruthenium (II) dichloride, and mixtures thereof.
10. A process to produce alpha-olefin comprising contacting a feed material (such as a feed oil) with the catalyst compound of any of paragraphs 1 to 9.
11. The process of paragraph 10, wherein the feed material is selected from the group consisting of canola oil, corn oil, soybean oil, rapeseed oil, algae oil, peanut oil, mustard oil, sunflower oil, tung oil, perilla oil, tall oil, grapeseed oil, linseed oil, safflower oil, pumpkin oil, palm oil, Jathropa oil, high-oleic soybean oil, high-oleic safflower oil, high-oleic sunflower oil, mixtures of animal and vegetable fats and oils, castor bean oil, dehydrated castor bean oil, cucumber oil, poppyseed oil, flaxseed oil, lesquerella oil, walnut oil, cottonseed oil, meadowfoam, tuna oil, sesame oils and mixtures thereof.
12. The process of paragraph 10, wherein the feed material is selected from the group consisting of tall oil, palm oil and algae oil.
13. A process to produce alpha-olefin comprising contacting a triacylglyceride with an alkene and the catalyst compound of any of paragraphs 1 to 9, preferably wherein the alpha olefin produced has at least one more carbon atom than the alkene.
14. The process of paragraph 13, wherein the triacylglyceride is contacted with alcohol and converted to a fatty acid ester or fatty acid alkyl ester prior to contacting with the catalyst compound of any of paragraphs 1 to 9.
15. The process of paragraph 13, wherein the triacylglyceride is contacted with water and/or an alkaline reagent and converted to a fatty acid prior to contacting with the catalyst compound of any of paragraphs 1 to 9.
16. A process to produce alpha-olefin comprising contacting an unsaturated fatty acid with an alkene and the catalyst compound of any of paragraphs 1 to 9, preferably wherein the alpha olefin produced has at least one more carbon atom than the alkene.
17. A process to produce alpha-olefin comprising contacting a triacylglyceride with the catalyst compound of any of paragraphs 1 to 9, preferably wherein the alpha olefin produced has at least one more carbon atom than the alkene.
18. A process to produce alpha-olefin comprising contacting an unsaturated fatty acid ester and or unsaturated fatty acid alkyl ester with an alkene and the catalyst compound of any of paragraphs 1 to 9, preferably wherein the alpha olefin produced has at least one more carbon atom than the alkene.
19. The process of any of paragraphs 11 to 18, wherein the alpha olefin is a linear alpha-olefin having 4 to 24 carbon atoms.
20. The process of any of paragraphs 11 to 19, wherein the alkene is ethylene, propylene, butene, hexene, or octene.
21. The process of any of paragraphs 19 to 20, wherein the fatty acid ester is a fatty acid methyl ester.
22. The process of any of paragraphs 13 to 21, wherein the triacylglyceride, fatty acid, fatty acid alkyl ester, fatty acid ester is derived from biodiesel.
23. The process of any of paragraphs 10 to 22, wherein the alpha-olefin is butene-1, decene-1, and/or heptene-1.
24. The process of any of paragraphs 10 to 23, wherein the productivity of the process is at least 200 g of linear alpha-olefin per mmol of catalyst per hour.
25. The process of any of paragraphs 10 to 24, wherein the selectivity of the process is at least 20 wt % linear alpha-olefin, based upon the weight to the material exiting the reactor.
26. The process of any of paragraphs 10 to 25, wherein the turnover number of the process is at least 5,000.
27. The process of any of paragraphs 10 to 26, wherein the yield, when converting unsaturated fatty acids, unsaturated fatty acid esters, unsaturated fatty acid alkyl esters, or mixtures thereof, is 30% or more, said yield being defined as defined as the moles of alpha olefin formed per mol of unsaturated fatty acids, unsaturated fatty acid esters, unsaturated fatty acid alkyl esters, or mixtures thereof introduced into the reactor.
28. The process of any of paragraphs 10 to 26, wherein the yield, when converting TAGs as represented in the formula below, is 30% or more, said yield being defined as defined as the moles of alpha olefin formed divided by (the moles of unsaturated $R^a$+moles of unsaturated $R^b$+moles of unsaturated $R^c$) introduced into the reactor,

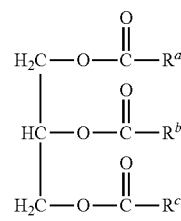

where $R^a$, $R^b$, and $R^c$ each, independently, represent a saturated or unsaturated hydrocarbon chain.
29. The process of paragraph 27, wherein the yield is 60% or more.
30. A process to produce $C_4$ to $C_{24}$ linear alpha-olefin comprising contacting a feed material with an alkene selected from the group consisting of ethylene, propylene butene, pentene, hexene, heptene, octene, nonene, decene, and mixtures thereof and a metathesis catalyst compound of any of paragraphs 1 to 10, wherein the feed material is a triacylglyceride, fatty acid, fatty acid alkyl ester, and/or fatty acid ester derived from seed oil.
31. The process of claim 30, wherein the alkene is ethylene, the alpha olefin is 1-butene, 1-heptene, and/or -decene, and the feed material is a fatty acid methyl ester, and/or fatty acid ester.

EXPERIMENTAL SECTION

Tests and Materials

All molecular weights are number average unless otherwise noted. All molecular weights are reported in g/mol unless otherwise noted.

For purposes of this invention and the claims thereto, Et is ethyl, Me is methyl, Ph is phenyl, Cy is cyclohexyl, THF is tetrahydrofuran, MeOH is methanol, DCM is dichloromethane, and TLC is thin layer chromatography.

Typical dry-box procedures for synthesis of air-sensitive compounds were followed including using dried glassware (90° C., 4 hours) and anhydrous solvents purchased from Sigma Aldrich (St. Louis, Mo.) which were further dried over 3 A sieves. All reagents were purchased from Sigma-Aldrich, unless otherwise noted. $^1$H, $^{13}$C, and $^{31}$P spectra were recorded on Bruker 250 and 500 spectrometers. IR data was recorded on Bruker Tensor 27 FT-IR spectrometer. Yields of metathesis product and catalyst turnover numbers were calculated from data recorded on an Agilent 6890 GC spectrometer as shown below.

Typically, a sample of the metathesis product will be taken and analyzed by GC. An internal standard, usually tetradecane, is used to derive the amount of metathesis product that is obtained. The amount of metathesis product is calculated from the area under the desired peak on the GC trace, relative to the internal standard.

Yield is reported as a percentage and is generally calculated as 100×[micromoles of metathesis products obtained by GC]/[micromoles of feed material weighed into reactor].

Selectivity is reported as a percentage and was calculated as 100×[area under the peak of desired metathesis products]/ [sum of peak areas of cross-metathesis and the homometathesis products].

Catalyst turnovers (TON) for production of the metathesis products is defined as the [micromoles of metathesis product]/([micromoles of catalyst].

In a particular embodiment, the metathesis of methyl oleate with ethylene will yield cross-metathesis products of 1-decene and methyl-9-decenoate. In addition to the desired products, the methyl oleate may homometathesize to produce small amounts of 9-octadecene, a less desirable product, and 1,18-dimethyl-9-octadecenedioate, a second less desirable product. Yield was calculated as 100×[micromoles of ethenolysis products obtained from the GC]/[micromoles of methyl oleate weighed into reactor]. 1-decene selectivity is shown as a percentage and was calculated as 100×[GC peak area of 1-decene & methyl-9-decenoate]/[sum of GC peak areas of 1-decene, methyl-9-decenoate, and the homometathesis products, 9-octadecene, and 1,18-dimethyl-9-octadecenedioate]. Catalyst turnovers for production of the 1-decene was calculated as the [micromoles of 1-decene obtained from the gas chromatograph]/([micromoles of catalyst].

Products were analyzed by gas chromatography (Agilent 6890N with auto-injector) using helium as a carrier gas at 38 cm/sec. A column having a length of 60 m (J & W Scientific DB-1, 60 m×0.25 mm I.D.×1.0 μm film thickness) packed with a flame ionization detector (FID), an Injector temperature of 250° C., and a Detector temperature of 250° C. were used. The sample injected into the column in an oven at 70° C., then heated to 275° C. over 22 minutes (ramp rate 10° C./minute to 100° C., 30° C./minute to 275° C., hold).

EXAMPLES

Example 1

Synthesis of Catalyst 1: (1-mesityl-3-methyl-2H-4,5-dihydroimidazol-2-ylidene)(tricyclohexylphosphine)-3-phenyl-1H-inden-1-ylideneruthenium(II) dichloride

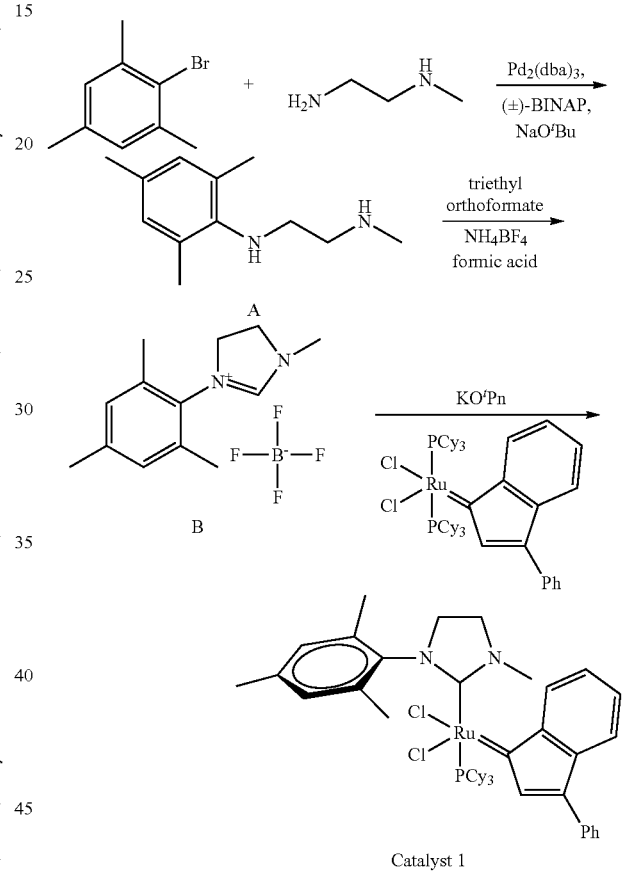

Catalyst 1

Synthesis of Compound A:
N-methyl-N'-mesityl-1,2-ethylenediamine

In a 100 mL round-bottom flask tris(dibenzylideneacetone)dipalladium(0) (Pd$_2$(dba)$_3$) (110 mg, 0.120 mmol) and (±)-2,2'-Bis(diphenylphosphino)-1,1'-binaphthalene ((±)-BINAP) (230 mg, 0.37 mmol) were added to 25 mL toluene and stirred for 20 minutes. Next, 2-bromomesitylene (2.45 g, 12.3 mmol), N-methylethylenediamine (1.01 g, 13.6 mmol) and sodium t-butoxide (NaO$^t$Bu) (3.56 g, 37 mmol) were added along with 25 mL toluene. This was stirred for 72 hours at 80° C. The flask was then removed from heat, cooled to room temperature and diluted with 20 mL diethyl ether. The solution was then washed with 5×30 mL water and 3×15 mL brine, and dried over magnesium sulfate. After filtering and vacuum removal of solvent, a dark red oil was recovered and used without further purification.

Synthesis of Compound B: 1-Mesityl-3-methyl-2H-4,5-dihydroimidazolium tetrafluoroborate Compound A (2.07 g, 10.8 mmol) oil was diluted in 10 mL toluene and stirred with triethylorthoformate (15.98 g, 108 mmol), ammonium tetrafluoroborate ($NH_4BF_4$) (4.51 g, 43 mmol) and 5 drops of formic acid at 130° C. for 18 hours. After cooling to room temperature the solution was filtered and solids were dissolved in dichloromethane and precipitate filtered off. The solvent was removed by purging with nitrogen and the residue was recrystallized from acetone/methyl tert-butyl ether. A total of 0.39 g (25.1%) of Compound B was obtained.

Synthesis of Catalyst 1: (1-mesityl-3-methyl-2H-4,5-dihydroimidazol-2-ylidene)(tricyclohexylphosphine)-3-phenyl-1H-inden-1-ylideneruthenium(II) dichloride To a solution of Compound B (50 mg, 0.172 mmol) in 5 mL hexanes was added potassium tert-pentoxide (KO$^t$Pn) (0.172 mmol) from a 15% solution in hexanes. To this solution was added bis(tricyclohexylphosphine)-3-phenyl-1H-inden-1-ylideneruthenium (II) dichloride (purchased from Strem Chemicals, (Newburyport, Mass.)) (145 mg, 0.156 mmol) and the solution then stirred for 12 hours at 50° C. After cooling to room temperature, the solution was concentrated to approximately 2 mL under a stream of nitrogen, then filtered and washed with hexanes, yielding 105 mg (79%) of Catalyst 1 as a brown powder.

Methyl Oleate Ethynolysis (Cross-Metathesis of Methyl Oleate with Ethylene):

Catalyst 1: The ethynolysis of methyl oleate was used as a test to determine the activity of the (1-mesityl-3-methyl-2H-4,5-dihydroimidazol-2-ylidene)(tricyclohexylphosphine)-3-phenyl-1H-inden-1-ylideneruthenium(II) dichloride complex (Catalyst 1). A 0.120 mM stock solution was made by dissolving Catalyst 1 in dichloromethane. Methyl oleate (0.87 g, 1.0 mL), Catalyst 1 stock solution (125 nmol, 1.04 mL), dichloromethane (2.91 mL) and of tetradecane (0.152 g, used as an internal standard) were weighed out and then placed in a Fisher-Porter bottle equipped with a stir bar. The Fisher-Porter bottle was then filled with ethylene to 150 psig and placed in an oil bath heated to 40° C. for 3 hours. The vessel was depressurized and 5 drops of ethyl vinyl ether was added to stop the reaction. A sample was removed and analyzed by GC.

Comparative Catalyst A: Tricyclohexylphosphine[3-phenyl-1H-inden-1-ylidene][1,3-bis(2,4,6-trimethylphenyl)-4,5-dihydroimidazol-2-ylidene]ruthenium(II) dichloride (Comparative Catalyst A) is a symmetrical annolog of Catalyst 1 and was purchased from Strem Chemicals. The structure of Comparative Catalyst A is shown below.

Comparative Catalyst A

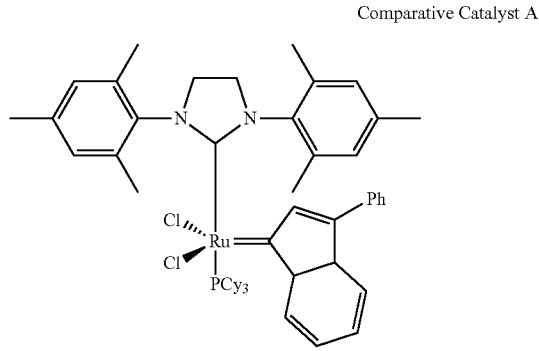

A 0.139 mM solution of the Comparative Catalyst A complex in dichloromethane was prepared. Comparative Catalyst A stock solution (94.4 nmol, 0.679 mL), dichloromethane (3.12 mL), methyl oleate (0.87 g, 1.0 mL) and tetradecane (0.152 g, used as an internal standard) were weighed out and then placed in a Fisher-Porter bottle equipped with a stir bar. The Fisher-Porter bottle was filled with 150 psig of ethylene and heated to 40° C. for 3 hours. A sample was removed and analyzed by GC.

The results of the ethenolysis reactions are as follows:

| Catalyst | nmols Catalyst | % selectivity | % yield | TON (1-Decene) |
|---|---|---|---|---|
| Catalyst 1 | 125 | 91.2 | 28.6 | 6700 |
| Comparative Catalyst A | 94.4 | 89.8 | 3.84 | 1200 |

In the ethenolysis of methyl oleate, symmetrically substituted NHC carbene ligands ligated to ruthenium alkylidenes, such as tricyclohexylphosphine[3-phenyl-1H-inden-1-ylidene][1,3-bis(2,4,6-trimethylphenyl)-4,5-dihydroimidazol-2-ylidene]ruthenium(II) dichloride (Comparative Catalyst A), have displayed low activity resulting in comparatively low yields of 3.84% with correspondingly low turnover numbers of 1200.

The inventors have surprisingly discovered that by replacing one of the mesityl groups on the nitrogen of the NHC ligand ligated to the ruthenium alkylidene, as in Catalyst 1 above, the activity increased substantially as depicted by increased turnover numbers in excess of five-fold, with a corresponding increase in yield.

Example 2

Synthesis of Catalyst 2: 2-(i-propoxy)-5-(N,N-dimethylaminosulfonyl)phenyl]methylene}(1-cyclohexylmethyl-3-(2,6-diisopropylphenyl)-4,5-dihydro-1H-imidazole) ruthenium (II) chloride

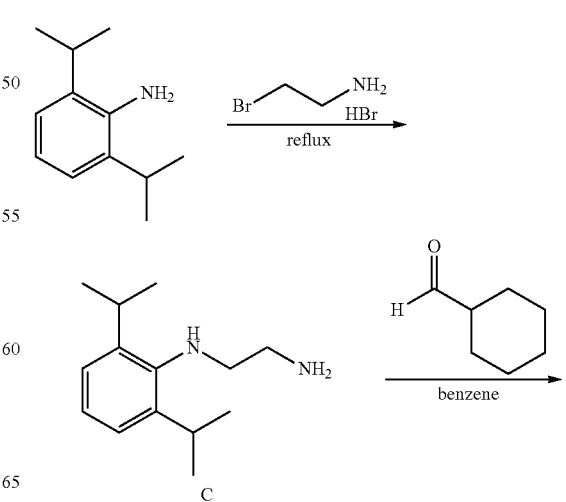

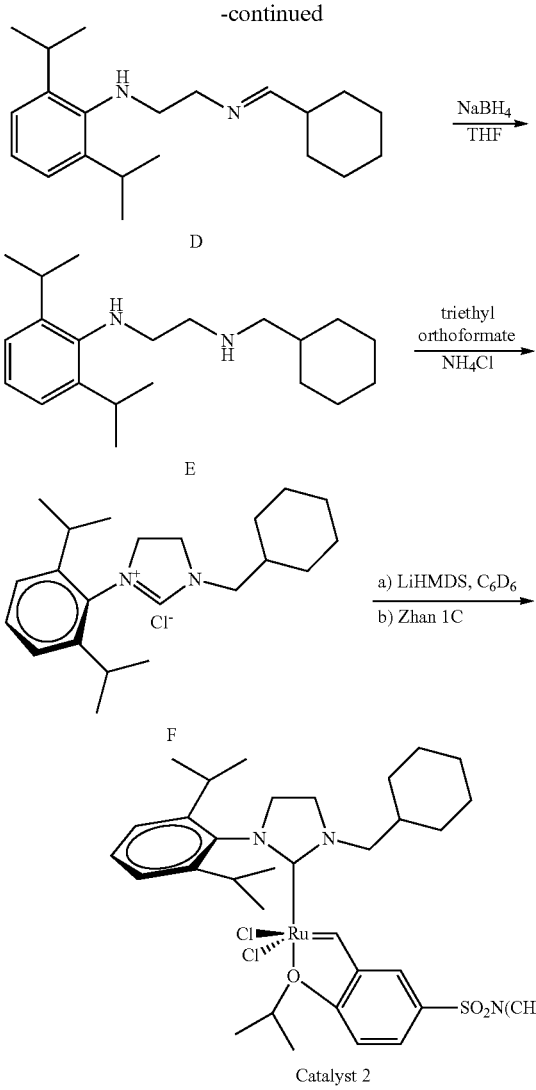

Synthesis of Compound C: N¹-(2,6-diisopropylphenyl)ethane-1,2-diamine 2,6-Diisopropylaniline (12 mL, 63.6 mmol) and 2-bromoethylamine hydrobromide (2.8 g, 14 mmol) were heated at reflux for 4 days. The liquid was cooled to room temperature and dissolved in ether. This solution was washed with 1N sodium hydroxide and brine, then dried over magnesium sulfate, filtered and concentrated under reduced pressure. Unreacted diisopropylaniline was removed by vacuum distillation, followed by column chromatography with 30% acetone/hexane eluent. The pure diamine product, Compound A, was obtained as a pale yellow oil in quantitative yield: $R_f$ 0.31 (30:70 acetone/hexane); IR (cm$^{-1}$): 3359, 2961, 2868, 1667, 1458, 1364, 1252, 1113, 755; $^1$H NMR (500 MHz, C$_6$D$_6$) δ 1.29 (m, 12H), 1.79 (s, 2H), 3.14 (br s, 2H), 3.18 (m, 2H), 3.67 (qn, J=10 Hz, 2H), 4.07 (br s, 1H), 7.14 (m, 3H); $^{13}$C NMR (125 MHz, C$_6$D$_6$) 24.5 (4C), 27.8 (2C), 51.2, 52.7, 123.8, 124.1, 143.0, 144.5, 166.8.

Synthesis of Compound D: N¹-cyclohexylmethylene-N²-(2,6-diisopropylphenyl)ethane-1,2-diamine Compound C (2.3 g, 10.4 mmol) and cyclohexylcarboxaldehyde (1.3 mL, 11 mmol) were dissolved in 20 mL benzene and refluxed for 1.5 hours, as water was collected in a Dean-Stark trap. The reaction was cooled and benzene removed under reduced pressure to give Compound D as a pale yellow oil, which was carried on to the next step without further purification.

Synthesis of Compound E: N¹-cyclohexylmethyl-N²-(2,6-diisopropylphenyl)ethane-1,2-diamine Compound D was dissolved in 50 mL THF. Sodium borohydride (NaBH$_4$) (1.9 g, 50 mmol) was added in portions. The reaction was allowed to reflux for 30 minutes, then cooled and quenched with methanol. Water was added, and then the mixture was concentrated and extracted with 3 portions of dichloromethane. The combined organic layers were washed with brine, dried over magnesium sulfate, and concentrated under reduced pressure. A crude yellow oil (Compound E) was obtained in 65% yield: $R_f$ 0.46 (30:70 acetone/hexane); IR (cm$^{-1}$): 3359, 2960, 2924, 2851, 1447, 1362, 1254, 1111, 754; $^1$H NMR (250 MHz, C$_6$D$_6$) δ 1.23 (m, 20H), 1.67 (m, 5H), 2.30 (d, J=6.5 Hz, 2H), 2.60 (m, 2H), 2.92 (m, 2H), 3.54 (qn, J=6.8 Hz, 2H), 7.14 (m, 3H).

Synthesis of Compound F: 1-cyclohexylmethyl-3-(2,6-diisopropylphenyl)-4,5-dihydro-1H-imidazol-3-ium chloride Compound E (2 g, 6.3 mmol) was dissolved in 20 mL triethylorthoformate. Ammonium chloride (360 mg, 6.6 mmol) was added and the reaction heated at reflux overnight, during which, it turned dark red and a precipitate formed. The mixture was cooled and filtered. Washing the solid with ether gave Compound F as a tan powder in 52% yield:

$^1$H NMR (250 MHz, CDCl$_3$/DMSO) δ 1.09 (m, 18H), 1.60 (m, 5H), 2.27 (qn, J=6.8 Hz, 2H), 3.64 (d, J=7.3 Hz, 2H), 4.09 (m, 4H), 7.08 (d, J=7.5 Hz, 2H), 7.27 (m, 1H), 9.63 (s, 1H);

$^{13}$C NMR (63 MHz, CDCl$_3$/DMSO) 23.5-25.5 (7C), 28.5 (2C), 29.5 (2C), 34.5, 48.7, 53.0, 53.6, 124.4 (2C), 129.7, 130.6, 146.2 (2C), 159.5.

Synthesis of Catalyst 2: 2-(i-propoxy)-5-(N,N-dimethylaminosulfonyl)phenyl]methylene}(1-cyclohexylmethyl-3-(2,6-diisopropylphenyl)-4,5-dihydro-1H-imidazole) ruthenium (II) chloride An oven dried 20 mL scintillation vial was charged with LiHMDS (lithium bistrimethylsilylamide) (40 mg, 0.24 mmol) and dissolved in 4 mL C$_6$D$_6$. Compound F (88 mg, 0.24 mmol) was then added portion wise over 5 minutes. This mixture was allowed to stir for about 30 minutes until the solid ligand was mostly dissolved. Zhan 1C (2-(i-propoxy)-5-(N,N-dimethylaminosulfonyl)phenylmethylene(tricyclohexylphosphine) ruthenium dichloride) (114 mg, 0.16 mmol) was then added in one portion and the mixture was allowed to stir at room temperature. After 1 hour, CuCl (copper (I) chloride) (160 mg, 1.6 mmol) was added and allowed to stir overnight. The reaction mixture was loaded directly onto a silica column (loaded in 50% DCM/hexane) and eluted with 1% MeOH/DCM. The pure fractions were concentrated in vacuo, yielding approximately 50 mg of Catalyst 2.

Example 3

Synthesis of Catalyst 3

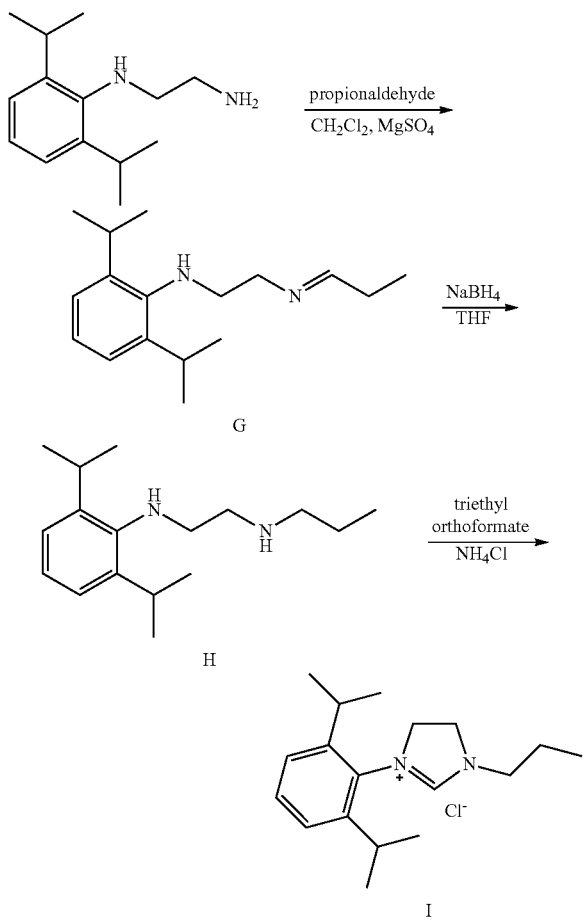

Synthesis of Compound G: N¹-2,6-diisopropylphenyl-N²-propylideneethane-1,2-diamine Propionaldehyde (0.6 mL, 8.3 mmol) and 2,6-diisopropylphenylethane-1,2-diamine (1.5 g, 6.8 mmol) were dissolved in 20 mL dichloromethane. Magnesium sulfate was added and the mixture stirred for 19 hours, then filtered and concentrated. Compound G was obtained as a crude yellow oil which was carried on to the next step without further purification.

Synthesis of Compound H: N¹-2,6-diisopropylphenyl-N²-propylethane-1,2-diamine Compound G was dissolved in 30 mL THF. Sodium borohydride (NaBH$_4$) (1.3 g, 34 mmol) was added in portions. The reaction was allowed to reflux for 30 minutes, then cooled and quenched with methanol. Water was added, and then the mixture was concentrated and extracted with 3 portions of dichloromethane. The combined organic layers were washed with brine, dried over magnesium sulfate, and concentrated under reduced pressure. Compound H was obtained as a crude pale yellow oil in 35% yield: $^1$H NMR (250 MHz, C$_6$D$_6$) δ 0.85 (t, J=7.3 Hz, 3H), 1.26 (m, 14H), 2.36 (t, J=6.9 Hz, 2H), 2.58 (m, 2H), 2.90 (m, 2H), 3.52 (qn, J=6.8 Hz, 2H), 7.12 (m, 3H).

Synthesis of Compound I: 3-(2,6-diisopropylphenyl)-1-propyl-4,5-dihydro-1H-imidazol-3-ium chloride Compound H (650 mg, 2.4 mmol) was dissolved in 7.9 mL triethylorthoformate. Ammonium chloride (NH$_4$Cl) (141 mg, 2.64 mmol) was added and the reaction heated at reflux overnight. Removal of triethylorthoformate gave Compound I as a crude reddish brown oil in quantitative yield.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What we claim is:

1. A metathesis catalyst compound represented by the formula:

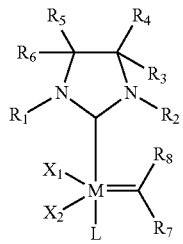

where:

M is a Group 8 metal;

$X_1$ and $X_2$ are, independently, any anionic ligand, or $X_1$ and $X_2$ may be joined to form a dianionic group and may form a single ring of up to 30 non-hydrogen atoms or a multinuclear ring system of up to 30 non-hydrogen atoms;

L may be joined to $R_7$ and/or $R_8$ and is $L^*(R)_{q-1}$ when L is not bound to $R_7$ or $R_8$ or L is $L^*(R)_{q-2}$ when L is bound to $R_7$ or $R_8$, where q is 1, 2, 3, or 4 depending on the valence of L* (which may be 2, 3, 4, or 5) and L* is N, O, P, or S, and R is hydrogen or a $C_1$ to $C_{30}$ substituted or unsubstituted hydrocarbyl;

$R_3$, $R_4$, $R_5$, $R_6$, $R_7$, and $R_8$ are, independently, hydrogen or a $C_1$ to $C_{30}$ substituted or unsubstituted hydrocarbyl;

wherein any two adjacent R groups may form a single ring of up to 8 non-hydrogen atoms or a multinuclear ring system of up to 30 non-hydrogen atoms;

$R_1$ is a substituted phenyl; and $R_2$ is n-butyl, pentyl, hexyl, or cyclohexylmethyl;

provided that when $R_7$ and $R_8$ form an unsubstituted phenyl group and $R_1$ is mesityl, then $R_2$ is pentyl, hexyl, or cyclohexylmethyl.

2. The catalyst compound of claim 1, wherein M is ruthenium.

3. The catalyst compound of claim 1, wherein $X_1$ and $X_2$ are, independently, a halogen, an alkoxides, or an alkyl sulfonate.

4. The catalyst compound of claim 1, wherein L* is P and R is selected from the group consisting of methyl, ethyl, propyl butyl, hexyl, octyl, nonyl, decyl, undecyl, dodecyl, indenylene, substituted indenylene, phenyl, substituted phenyl, and the linear, branched and cyclic isomers thereof.

5. The catalyst compound of claim 1, wherein L* is N, O, or P.

6. A metathesis catalyst compound represented by the formula:

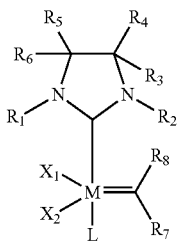

where:
M is a Group 8 metal;
$X_1$ and $X_2$ are, independently, any anionic ligand, or $X_1$ and $X_2$ may be joined to form a dianionic group and may form a single ring of up to 30 non-hydrogen atoms or a multinuclear ring system of up to 30 non-hydrogen atoms;
L may be joined to $R_7$ and/or $R_8$ and is $L^*(R)_{q-1}$ when L is not bound to $R_7$ or $R_8$ or L is $L^*(R)_{q-2}$ when L is bound to $R_7$ or $R_8$, where q is 1, 2, 3, or 4 depending on the valence of L* (which may be 2, 3, 4, or 5) and L* is N, O, P, or S, and R is hydrogen or a $C_1$ to $C_{30}$ substituted or unsubstituted hydrocarbyl;
$R_3$, $R_4$, $R_5$, and $R_6$, are hydrogen;
$R_7$, and $R_8$ are, independently, hydrogen or a $C_1$ to $C_{30}$ substituted or unsubstituted hydrocarbyl;
wherein any two adjacent R groups may form a single ring of up to 8 non-hydrogen atoms or a multinuclear ring system of up to 30 non-hydrogen atoms;
$R_1$ is a substituted phenyl; and
$R_2$ is n-propyl, n-butyl, pentyl, hexyl, or cyclohexylmethyl;
provided that when $R_7$ and $R_8$ form an unsubstituted phenyl group and $R_1$ is mesityl, then $R_2$ is pentyl, hexyl, or cyclohexylmethyl.

7. A metathesis catalyst compound represented by the formula:

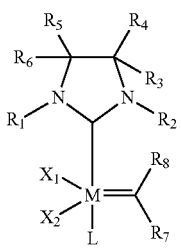

where:
M is a Group 8 metal;
$X_1$ and $X_2$ are, independently, any anionic ligand, or $X_1$ and $X_2$ may be joined to form a dianionic group and may form a single ring of up to 30 non-hydrogen atoms or a multinuclear ring system of up to 30 non-hydrogen atoms;

L may be joined to $R_7$ and/or $R_8$ and is $L^*(R)_{q-1}$ when L is not bound to $R_7$ or $R_8$ or L is $L^*(R)_{q-2}$ when L is bound to $R_7$ or $R_8$, where q is 1, 2, 3, or 4 depending on the valence of L* (which may be 2, 3, 4, or 5) and L* is N, O, P, or S, and R is hydrogen or a $C_1$ to $C_{30}$ substituted or unsubstituted hydrocarbyl;
$R_3$, $R_4$, $R_5$, $R_6$, $R_7$, and $R_8$ are, independently, hydrogen or a $C_1$ to $C_{30}$ substituted or unsubstituted hydrocarbyl;
wherein any two adjacent R groups may form a single ring of up to 8 non-hydrogen atoms or a multinuclear ring system of up to 30 non-hydrogen atoms;
each $R_1$ is 2,6 diisopropylphenyl; and
$R_2$ is n-propyl, n-butyl, pentyl, hexyl, or cyclohexylmethyl;
provided that when $R_7$ and $R_8$ form an unsubstituted phenyl group and $R_1$ is mesityl, then $R_2$ is pentyl, hexyl, or cyclohexylmethyl.

8. The catalyst compound of claim 2, wherein L* is P.

9. A metathesis catalyst compound comprising one or more of: 2-(i-propoxy)-5-(N,N-dimethylaminosulfonyl) phenylmethylene(1-cyclohexylmethyl-3-(2,6-diisopropylphenyl)-4, 5-dihydro-1H-imidazole)ruthenium (II) dichloride, (1-mesityl-3-methyl-2H-4,5 - dihydroimidazol-2-ylidene)(tricyclohexylpho sphine)-3-phenyl-1H-inden-1-ylidene ruthenium (II) dichloride, and mixtures thereof.

10. A process to produce alpha-olefin comprising contacting a feed material with a metathesis catalyst compound represented by the formula:

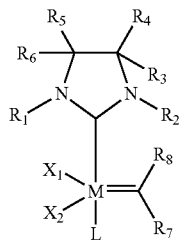

where:
M is a Group 8 metal;
$X_1$ and $X_2$ are, independently, any anionic ligand, or $X_1$ and $X_2$ may be joined to form a dianionic group and may form a single ring of up to 30 non-hydrogen atoms or a multinuclear ring system of up to 30 non-hydrogen atoms;
L may be joined to $R_7$ and/or $R_8$ and is $L^*(R)_{q-1}$ when L is not bound to $R_7$ or $R_8$ or L is $L^*(R)_{q-2}$ when L is bound to $R_7$ or $R_8$, where q is 1, 2, 3, or 4 depending on the valence of L* (which may be 2, 3, 4, or 5) and L* is N, O, P, or S, and R is hydrogen or a $C_1$ to $C_{30}$ substituted or unsubstituted hydrocarbyl;
and $R_3$, $R_4$, $R_5$, $R_6$, $R_7$, and $R_8$ are, independently, hydrogen or a $C_1$ to $C_{30}$ substituted or unsubstituted hydrocarbyl;
wherein any two adjacent R groups may form a single ring of up to 8 non-hydrogen atoms or a multinuclear ring system of up to 30 non-hydrogen atoms;
$R_1$ is a substituted phenyl; and
$R_2$ is n-butyl, pentyl, hexyl, or cyclohexylmethyl;
provided that when $R_7$ and $R_8$ form an unsubstituted phenyl group and $R_1$ is mesityl, then $R_2$ is pentyl, hexyl, or cyclohexylmethyl.

11. The process of claim 10, wherein the feed material is a feed oil is selected from the group consisting of canola oil, corn oil, soybean oil, rapeseed oil, algae oil, peanut oil, mustard oil, sunflower oil, tung oil, perilla oil, tall oil, grapeseed oil, linseed oil, safflower oil, pumpkin oil, palm oil, Jathropa oil, high-oleic soybean oil, high-oleic safflower oil, high-oleic sunflower oil, tall oil, mixtures of animal and vegetable fats and oils, castor bean oil, dehydrated castor bean oil, cucumber oil, poppyseed oil, flaxseed oil, lesquerella oil, walnut oil, cottonseed oil, meadowfoam, tuna oil, sesame oils and mixtures thereof.

12. The process of claim 10, wherein the feed material is selected from the group consisting of tall oil, palm oil and algae oil.

13. A process to produce alpha-olefin comprising contacting a triacylglyceride with an alkene and a metathesis catalyst compound represented by the formula:

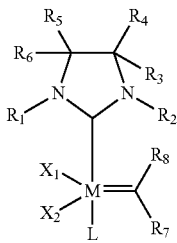

where:

M is a Group 8 metal;

$X_1$ and $X_2$ are, independently, any anionic ligand, or $X_1$ and $X_2$ may be joined to form a dianionic group and may form a single ring of up to 30 non-hydrogen atoms or a multinuclear ring system of up to 30 non-hydrogen atoms;

L may be joined to $R_7$ and/or $R_8$ and is $L^*(R)_{q-1}$ when L is not bound to $R_7$ or $R_8$ or L is $L^*(R)_{q-2}$ when L is bound to $R_7$ or $R_8$, where q is 1, 2, 3, or 4 depending on the valence of $L^*$ (which may be 2, 3, 4, or 5) and $L^*$ is N, O, P, or S, and R is hydrogen or a $C_1$ to $C_{30}$ substituted or unsubstituted hydrocarbyl;

and $R_3$, $R_4$, $R_5$, $R_6$, $R_7$, and $R_8$ are, independently, hydrogen or a $C_1$ to $C_{30}$ substituted or unsubstituted hydrocarbyl;

wherein any two adjacent R groups may form a single ring of up to 8 non-hydrogen atoms or a multinuclear ring system of up to 30 non-hydrogen atoms;

$R_1$ is a substituted phenyl; and $R_2$ is n-butyl, pentyl, hexyl, or cyclohexylmethyl;

provided that when $R_7$ and $R_8$ form an unsubstituted phenyl group and $R_1$ is mesityl, then $R_2$ is pentyl, hexyl, or cyclohexylmethyl.

14. The process of claim 13, wherein the triacylglyceride is contacted with alcohol and converted to an fatty acid ester or fatty acid alkyl ester prior to contacting with the catalyst compound.

15. The process of claim 13, wherein the triacylglyceride is contacted with water and converted to a fatty acid prior to contacting with the catalyst compound.

16. A process to produce alpha-olefin comprising contacting an unsaturated fatty acid with an alkene and the catalyst compound of claim 1, wherein the process is a homogeneous process.

17. A process to produce alpha-olefin comprising contacting a triacylglyceride with the catalyst compound of claim 1, wherein the process is a homogeneous process.

18. A process to produce alpha-olefin comprising contacting an unsaturated fatty acid ester and/or unsaturated fatty acid alkyl ester with an alkene and the catalyst compound of claim 1, wherein the process is a homogeneous process.

19. The process of claim 18, wherein the alpha olefin is a linear alpha-olefin having 4 to 24 carbon atoms.

20. The process of claim 18, wherein the alkene is ethylene, propylene, butene, hexene, or octene.

21. The process of claim 18, where the fatty acid alkyl ester is a fatty acid methyl ester.

22. A process to produce alpha-olefin comprising contacting a feed material with an alkene and a metathesis catalyst compound represented by the formula:

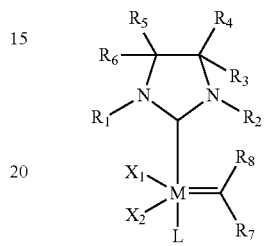

where:

M is a Group 8 metal;

$X_1$ and $X_2$ are, independently, any anionic ligand, or $X_1$ and $X_2$ may be joined to form a dianionic group and may form a single ring of up to 30 non-hydrogen atoms or a multinuclear ring system of up to 30 non-hydrogen atoms;

L may be joined to $R_7$ and/or $R_8$ and is $L^*(R)_{q-1}$ when L is not bound to $R_7$ or $R_8$ or L is $L^*(R)_{q-2}$ when L is bound to $R_7$ or $R_8$, where q is 1, 2, 3, or 4 depending on the valence of $L^*$ (which may be 2, 3, 4, or 5) and $L^*$ is N, O, P, or S, and R is hydrogen or a $C_1$ to $C_{30}$ substituted or unsubstituted hydrocarbyl;

and $R_3$, $R_4$, $R_5$, $R_6$, $R_7$, and $R_8$ are, independently, hydrogen or a $C_1$ to $C_{30}$ substituted or unsubstituted hydrocarbyl;

wherein any two adjacent R groups may form a single ring of up to 8 non-hydrogen atoms or a multinuclear ring system of up to 30 non-hydrogen atoms;

$R_1$ is a substituted phenyl; and $R_2$ is n-butyl, pentyl, hexyl, or cyclohexylmethyl;

provided that when $R_7$ and $R_8$ form an unsubstituted phenyl group and $R_1$ is mesityl, then $R_2$ is pentyl, hexyl, or cyclohexylmethyl.

23. The process of claim 18, wherein the alpha-olefin is butene-1, decene-1, and/or heptene-1.

24. The process of claim 13, wherein the productivity of the process is at least 200 g of linear alpha-olefin per mmol of catalyst per hour.

25. The process of claim 13, wherein the selectivity of the process is at least 20 wt % linear alpha-olefin, based upon the weight to the material exiting the reactor.

26. The process of claim 13, wherein the turnover number, defined as the moles of alpha olefin formed per mol of catalyst, of the process is at least 5,000.

27. The process of claim 13, wherein the yield, when converting unsaturated fatty acids, unsaturated fatty acid esters, unsaturated fatty acid alkyl esters, or mixtures thereof, is 30% or more, said yield being defined as the moles of alpha olefin formed per mol of unsaturated fatty acids, unsaturated fatty acid esters, unsaturated fatty acid alkyl esters, or mixtures thereof introduced into the reactor.

28. The process of claim 13, wherein the yield, when converting triacylglycerides as represented in the formula below, is 30% or more, said yield being defined as defined as the moles of alpha olefin formed divided by (the moles of unsaturated $R^a$+moles of unsaturated $R^b$+moles of unsaturated $R^c$) introduced into the reactor,

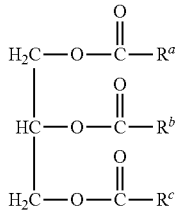

where $R^a$, $R^b$, and $R^c$ each, independently, represent a saturated or unsaturated hydrocarbon chain.

29. The process of claim 27, wherein the yield is 60% or more.

30. A process to produce $C_4$ to $C_{24}$ linear alpha-olefin comprising contacting a feed material with an alkene selected from the group consisting of ethylene, propylene, butene, pentene, hexene, heptene, octene, nonene, decene, and mixtures thereof and a metathesis catalyst compound represented by the formula:

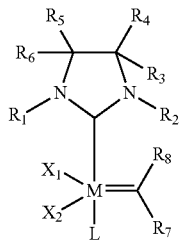

where:

M is a Group 8 metal $X_1$ and $X_2$ are, independently, any anionic ligand, or $X_1$ and $X_2$ may be joined to form a dianionic group and may form a single ring of up to 30 non-hydrogen atoms or a multinuclear ring system of up to 30 non-hydrogen atoms;

L may be joined to $R_7$ and/or $R_8$ and is $L^*(R)_{q-1}$ when L is not bound to $R_7$ or $R_8$ or L is $L^*(R)_{q-2}$ when L is bound to $R_7$ or $R_8$, where q is 1, 2, 3, or 4 depending on the valence of $L^*$ (which may be 2, 3, 4, or 5) and $L^*$ is N, O, P, or S, and R is hydrogen or a $C_1$ to $C_{30}$ substituted or unsubstituted hydrocarbyl;

and $R_4$, $R_5$, $R_6$, $R_7$, and $R_8$ are, independently, hydrogen or a $C_1$ to $C_{30}$ substituted or unsubstituted hydrocarbyl;

wherein any two adjacent R groups may form a single ring of up to 8 non-hydrogen atoms or a multinuclear ring system of up to 30 non-hydrogen atoms;

$R_1$ is a substituted phenyl;

$R_2$ is n-butyl, pentyl, hexyl, or cyclohexylmethyl;

provided that when $R_7$ and $R_8$ form an unsubstituted phenyl group and $R_1$ is mesityl, then $R_2$ is pentyl, hexyl, or cyclohexylmethyl; and wherein the feed material is a triacylglyceride, fatty acid, fatty acid alkyl ester, and/or fatty acid ester derived from seed oil.

31. The process of claim 30, wherein the alkene is ethylene, the alpha olefin is 1-butene, 1-heptene, and/or 1-decene, and the feed material is a fatty acid methyl ester, and/or fatty acid ester.

32. The catalyst composition of claim 1 wherein $L^*$ is P and R is selected from mesityl, 3,5,5-trimethylhexyl, cyclohexyl, methyl cyclohexyl, cyclododecyl, diisopropylphenyl, cyclopentyl, and norbornyl.

* * * * *